(12) United States Patent
Vishwakarma et al.

(10) Patent No.: US 9,932,327 B2
(45) Date of Patent: Apr. 3, 2018

(54) ROHITUKINE ANALOGS AS CYCLIN-DEPENDENT KINASE INHIBITORS AND A PROCESS FOR THE PREPARATION THEREOF

(71) Applicant: COUNCIL OF SCIENTIFIC AND INDUSTRIAL RESEARCH, Anusandhan Bhawan, Rafi Marg, New Delhi (IN)

(72) Inventors: Ram A. Vishwakarma, Jammu (IN); Sandip B. Bharate, Jammu (IN); Shashi Bhushan, Jammu (IN); Dilip M. Mondhe, Jammu (IN); Shreyans K. Jain, Jammu (IN); Samdarshi Meena, Jammu (IN); Santosh K. Guru, Jammu (IN); Anup S. Pathania, Jammu (IN); Suresh Kumar, Jammu (IN); Akanksha Behl, Jammu (IN); Mubashir J. Mintoo, Jammu (IN); Sonali S. Bharate, Jammu (IN); Prashant Joshi, Jammu (IN)

(73) Assignee: The Council of Scientific & Industrial Research, New Delhi (IN)

( * ) Notice: Subject to any disclaimer, the term of this patent is extended or adjusted under 35 U.S.C. 154(b) by 59 days.

(21) Appl. No.: 14/784,489

(22) PCT Filed: Apr. 16, 2014

(86) PCT No.: PCT/IN2014/000239
§ 371 (c)(1),
(2) Date: Oct. 14, 2015

(87) PCT Pub. No.: WO2014/170914
PCT Pub. Date: Oct. 23, 2014

(65) Prior Publication Data
US 2016/0052915 A1    Feb. 25, 2016

(30) Foreign Application Priority Data
Apr. 17, 2013   (IN) ............. 1142/DEL/2013

(51) Int. Cl.
*C07D 405/04*    (2006.01)
*A61K 31/453*    (2006.01)
*C07D 405/14*    (2006.01)

(52) U.S. Cl.
CPC ......... *C07D 405/04* (2013.01); *C07D 405/14* (2013.01)

(58) Field of Classification Search
CPC .............. C07D 405/04; C07D 405/14
USPC .......................... 546/196; 514/320
See application file for complete search history.

(56) References Cited

U.S. PATENT DOCUMENTS

| | | | |
|---|---|---|---|
| 4,900,727 A | 2/1990 | Kattige et al. | |
| 5,284,856 A | 2/1994 | Naik et al. | |
| 5,733,920 A | 3/1998 | Mansuri et al. | |
| 5,849,733 A * | 12/1998 | Kim ............... | C07D 405/04 514/217.03 |

OTHER PUBLICATIONS

Kattige et al. "4H-benzopyran-4- . . . " CA109:37739 (1988).*
Naik et al. "Preparation and use . . . " CA114:61928 (1991).*
Patani et al. "Bioisosterism . . . " Chem. Rev. 96, 3147-3176 (1996).*
Rubini et al. "Synthesis of isosteri . . . " Tetrahedron 42(21) 6039-6045 (1986).*
Thornber "Isosterism and . . . " Chem. Soc. Rev. v.8 p. 563-580 (1979).*
International Search Report issued in PCT/IN2014/000239, dated Sep. 25, 2014.

* cited by examiner

Primary Examiner — Charanjit Aulakh
(74) Attorney, Agent, or Firm — Locke Lord LLP; Nicholas J. DiCeglie, Jr.

(57) ABSTRACT

The present invention relates to the rohitukine (5,7-dihydroxy-8-(3-hydroxy-1-methyl-piperidin-4-yl)-4H-chromen-4-ones) analogs of formula A and pharmaceutically acceptable salts thereof. In addition, the invention relates to pharmaceutically acceptable compositions comprising at least one such compound, and methods of using the compounds for treating or preventing various proliferative disorders such as melanoma, leukemia, breast cancer and prostate cancer etc. [insert Formula A here] wherein, n=0 or 1, when n=1, the dotted line indicates the double bond.

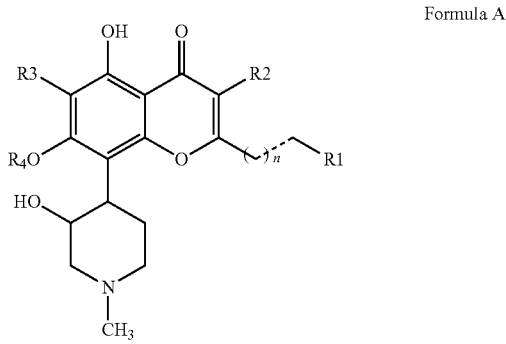

Formula A

7 Claims, 5 Drawing Sheets

(a)            (b)

SEQUENCE LISTING

<160> NUMBER OF SEQ ID NOS: 1

<210> SEQ ID NO 1
<211> LENGTH: 23
<212> TYPE: PRT
<213> ORGANISM: ARTIFICIAL SEQUENCE
<220> FEATURE:
<223> OTHER INFORMATION: RNA POLYMERASE

<400> SEQUENCE: 1

Tyr Ser Pro Thr Ser Pro Ser Tyr Ser Pro Thr Ser Pro Ser Tyr Ser
1               5                   10                  15

Pro Thr Ser Pro Lys Lys Lys
            20

ROHITUKINE ANALOGS AS CYCLIN-DEPENDENT KINASE INHIBITORS AND A PROCESS FOR THE PREPARATION THEREOF

CROSS REFERENCE TO RELATED APPLICATIONS

This application is a 35 U.S.C. § 371 National Phase Application of International PCT Patent Application No. PCT/IN2014/000239, filed Apr. 16, 2014 which application claims the benefit of priority to Indian Patent Application No. 1142/DEL/2013, filed Apr. 17, 2013, the contents of each of which in their entirety are hereby incorporated herein by reference.

FIELD OF THE INVENTION

The present invention relates to the 5,7-dihydroxy-8-(3-hydroxy-1-methylpiperidin-4-yl)-2-methyl-4H-chromen-4-one (Rohitukine) analogs that showed potent inhibition of cyclin-dependent kinase-2/cyclin A (CDK-2/cyclin A) and cyclin-dependent kinase-9/cyclin T1 (CDK-9/cyclin T1). These compounds are potent inhibitors of cell growth and proliferation, both in vitro as well as in vivo, and thus can be used to treat proliferative diseases such as cancer and other diseases involving abnormal cellular proliferation. As compounds of the present invention showed potent CDK-9 inhibition, these can be used for the treatment of HIV, rheumatoid arthritis, gout, type I diabetes, multiple sclerosis and cardiac hypertrophy. The present invention particularly relates to the preparation of semi-synthetic analogs of rohitukine (5,7-dihydroxy-8-(3-hydroxy-1-methylpiperidin-4-yl)-2-methyl-4H-chromen-4-one) and their CDK-2/A and CDK-9/T1 inhibitory effects.

BACKGROUND OF THE INVENTION

The disruption of any internal and external regulation of cellular growth leads to tumorogenesis by uncontrolled proliferation. This loss of control occurs at multiple levels in most of the cancer cases. Cyclin-dependent kinases (CDKs) have been recognized as key regulators of cell cycle progression. Alteration and deregulation of CDK activity have pathogenic link to the cancer. Number of cancers are associated with hyper-activation of CDKs as a result of mutation of the CDK genes or CDK inhibitor genes. Therefore, CDK inhibitors or modulators are of great interest to explore as novel therapeutic agents against cancer (Senderowicz, A. M. *Leukemia* 2001, 15, 1). Several classes of chemical inhibitors of CDK activity have been described (Zhang, J. et. al. *Nat Rev Cancer.* 2009, 9, 28) and some of them have reached to clinical pipeline for cancer.

Because CDK inhibitors are ATP competitive ligands; hence earlier they were typically described as purine class of compounds for example dimethylaminopurine, a first substance to be known as a CDK inhibitor (Neant, I. et al. *Exp. Cell Res.* 1988, 176, 68), olomoucine (Vesely, J. et al. *Eur. J. Biochem.* 1994, 224, 771) and roscovitine (Meijer, L. et al. *Eur. J. Biochem.* 1997, 243, 527). The $IC_{50}$ values of these purine class of compounds for CDK1/cyclin B are 120, 7 and 0.2-0.8 μM respectively (Gray, N. et al. *Curr. Med. Chem.* 1999, 6, 859). Some of the more potent members of this series have been prepared by the Schultz group using combinatorial approaches (Gray, N. S. et al. *Science* 1998, 281, 533). Number of synthetic flavoalkaloids having potent CDK inhibitory activity has been reviewed recently (Jain, S. K. et al. *Mini-Rev. Med. Chem.* 2012, 12, 632).

Specific CDKs operate in distinct phases of the cell cycle. CDK complexes with their respective type cyclin partners such as, complex of CDK2 and cyclin A is responsible for the cell's progression from G1 phase to S phase (Sherr, C. J. *Science* 1996, 274, 1672). DNA synthesis (S phase) begins with the CDK mediated phosphorylation of Rb (retinoblastoma) protein. Phosphorylated Rb is released from its complex with E2F. The released E2F then promotes the transcription of numerous genes required for the cell to progress through S phase, including thymidylate synthase and dihydrofolate reductase which are required for cell progression (Hatakeyama, M. et. al, *Cell Cycle Res.* 1995, 1, 9; Zhang, H. S. et. al. *Cell* 1999, 97, 53). Majority of human cancers have abnormalities in some component of the Rb pathway because of hyper-activation of CDKs resulting from the over-expression of positive cofactors (cyclins/CDKs) or a decrease in negative factors (endogenous CDK inhibitors) or Rb gene mutations (Sausville, E. A. et. al, *Pharmacol. Ther.* 1999, 82, 285).

The CDK-9 is a member of the Cdc2-like family of kinases. Its cyclin partners are members of the family of cyclin T (T1, T2a and T2b) and cyclin K. The CDK-9/cyclin T complexes appear to be involved in regulating several physiological processes. CDK9/cyclin T1 belongs to the P-TEFb complex, and is responsible for the phosphorylation of carboxyl terminal domain of the RNA Polymerase II, thus promoting general elongation. CDK-9 has also been described as the kinase of the TAK complex, which is homologous to the P-TEFb complex and is involved in HIV replication. CDK9 also appears to be involved in the differentiation program of several cell types, such as muscle cells, monocytes and neurons, suggesting that it may have a function in controlling specific differentiative pathways. In addition, CDK-9 seems to have an anti-apoptotic function in monocytes, that may be related to its control over differentiation of monocytes. This suggests the involvement of CDK-9 in several physiological processes in the cell, the deregulation of which may be related to the genesis of transforming events that may in turn lead to the onset of cancer. In addition, since the complex CDK-9/cyclin T1 is able to bind to the HIV-1 product Tat, the study of the functions of CDK-9/cyclin T may be of interest in understanding the basal mechanisms that regulate HIV replication (Falco, G. D. and Giordano A. *Cancer Biol. Therapy* 2002, 1, 337).

Rohitukine belongs to a class of chromone alkaloids and it was isolated by chemists at Hoechst India Ltd. in the early 1990's from *Dysoxylum binectariferum* Hook. which is phylogenetically related to the Ayurvedic plant, *D. malabaricum* Bedd., used for rheumatoid arthritis. Rohitukine was isolated as the constituent responsible for anti-inflammatory and immunomodulatory activity (Naik, R. G. et. al. *Tetrahedron* 1988, 44, 2081; U.S. Pat. No. 4,900,727, 1990). Medicinal chemistry efforts around this nature-derived flavone alkaloid led to discovery of two promising clinical candidates for treatment of cancer viz. flavopiridol of Sanofi-Aventis and P-276-00 of Piramal life sciences. Recently FDA has granted the orphan drug status to flavopiridol for treatment of chronic lymphocytic leukemia (CLL).

The molecular formula of rohitukine is $C_{16}H_{19}NO_5$ and the structure has a molecular weight of 305.32 g/mol. The chemical structure of rohitukine (1) is shown below. The present invention reports new semi-synthetic analogs of rohitukine as promising inhibitors of cyclin-dependent kinases such as CDK-2 and CDK-9.

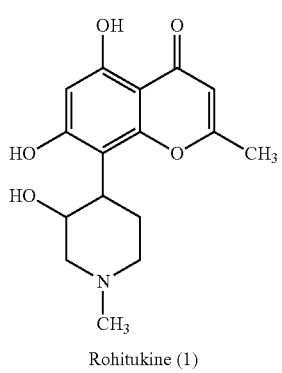 [SMILES: Cc1cc(=O)c2c(O)cc(O)c(C3CCN(C)CC3O)c2o1]

Rohitukine (1)

OBJECTIVES OF THE INVENTION

The main objective of the present invention is to provide novel analogue of 5, dihydroxy-8-(3-hydroxy-1-methylpiperidin-4-yl)-2-methyl-4H-chromen-4-one.

Yet another object of the present invention is to provide inhibitors of cyclin-dependent kinases, which are implicated in the pathogenesis of cancer and HIV infection.

Still another object of the present invention is to provide a process for the preparation of analogs of rohitukine.

Yet another objective of the present invention is to discover novel anticancer agents, exhibiting promising in vitro and in vivo tumor growth inhibition.

SUMMARY OF THE INVENTION

Accordingly, the present invention provides a compound of formula A and a pharmaceutically acceptable salt thereof, Formula A

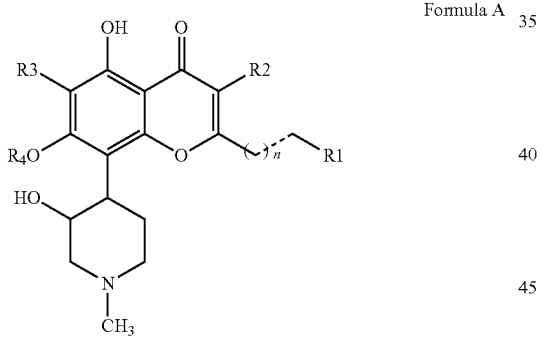

wherein,
n=0 or 1, when n=1, the dotted line indicates the double bond,
$R_1$ is selected from the group consisting of alkyl, substituted alkyl, alkyl having 1 to 6 carbon atoms, aryl, substituted aryl, fused aryl, heteroaryl, substituted heteroaryl, substitution on alkyl, aryl and heteroaryl with $C_1$-$C_4$-alkyl, halogen, nitro, amino, alkyl substituted amino, hydroxyl, alkoxy, carboxyl, COO-alkyl $C_1$-$C_4$ wherein alkyl is long chain or branched,
$R_2$ is hydrogen or

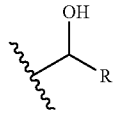

wherein R is selected from the group consisting of alkyl, substituted alkyl, alkyl having 1 to 15 carbon atoms with branched or unbranched, aryl, substituted aryl, fused aryl, heteroaryl, substituted heteroaryl, substitution on alkyl, aryl and heteroaryl with $C_1$-$C_4$-alkyl, halogen, nitro, amino, alkyl substituted amino, alkylamino, hydroxyl, alkoxy, carboxyl, ester groups,
wherein, alkyl group is selected from the group consisting of ($C_1$-$C_6$)-alkyl, ($C_1$-$C_4$)-haloalkyl, ($C_1$-$C_4$)-alkoxy, ($C_1$-$C_4$)-haloalkoxy, ($C_5$-$C_8$)-cycloalkyl, ($C_5$-$C_8$)-cycloalkenyl, ($C_6$-$C_{10}$)-bicycloalkyl, and ($C_6$-$C_{10}$)-bicycloalkenyl,
$R_3$ is selected from the group consisting of hydrogen, halogen, aryl, substituted aryl, heteroaryl, substituted heteroaryl, alkylamino, substitution on alkyl, aryl and heteroaryl with $C_1$-$C_4$-alkyl, halogen, nitro, amino, alkylamino, hydroxyl, alkoxy, carboxyl, ester groups,
wherein alkylamino group is selected from the group consisting of —NH-alkyl, N-dialkyl, NH-cycloalkyl, N-cycloalkyl, or, any alkyl substituted amino derived group derived from either amino acid or heterocycles,
$R_4$ is selected from the group consisting of hydrogen, alkyl, substituted alkyl, cycloalkyl, acyl, alkanoyl, alkenyl, benzyl, heteroaryl, —CO—$CH_2$-heteroaryl, —CO-Ph, —CO-substituted aryl, —CO-heteroaryl, or any carbon atom which may be optionally substituted; wherein, alkyl group may be selected from $C_1$-$C_{10}$ carbon chain or branched radical having up to 6 and preferably up to 5 carbon atoms, for example methyl, ethyl, propyl, isopropyl, t-butyl, pentyl, or isopentyl groups, substituted alkyl group is selected from $C_1$-$C_{10}$, containing one or more radical selected from the group consisting of halogen, nitro, amino, hydroxyl, cyano, phenyl, substituted phenyl, carboxyl and an aldehyde
wherein substituted phenyl is selected from the phenyls possessing substitutions at 2 to 5 positions with groups consisting of halogen, hydroxy, ($C_1$-$C_4$)-alkoxy, amino, nitro, cyano, carboxy.

In an embodiment of the present invention, said compound of formula A, comprising compound of formula I and compound of formula II

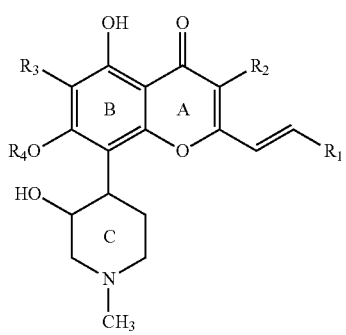

I

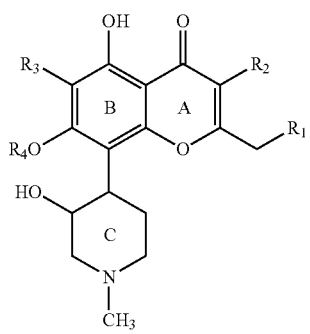

II wherein,
R₁ is selected from the group consisting of alkyl, substituted alkyl, alkyl having 1 to 6 carbon atoms, aryl, substituted aryl, fused aryl, heteroaryl, substituted heteroaryl, substitution on alkyl, aryl and heteroaryl with $C_1$-$C_4$-alkyl, halogen, nitro, amino, alkyl substituted amino, hydroxyl, alkoxy, carboxyl, COO-alkyl $C_1$-$C_4$ wherein alkyl is long chain or branched,
R₂ is hydrogen or

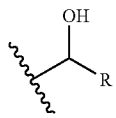

wherein R is selected from the group consisting of alkyl, substituted alkyl, alkyl having 1 to 15 carbon atoms with branched or unbranched, aryl, substituted aryl, fused aryl, heteroaryl, substituted heteroaryl, substitution on alkyl, aryl and heteroaryl with $C_1$-$C_4$-alkyl, halogen, nitro, amino, alkyl substituted amino, alkylamino, hydroxyl, alkoxy, carboxyl, ester groups,
wherein, alkyl group is selected from the group consisting of ($C_1$-$C_6$)-alkyl, ($C_1$-$C_4$)-haloalkyl, ($C_1$-$C_4$)-alkoxy, ($C_1$-$C_4$)-haloalkoxy, ($C_5$-$C_8$)-cycloalkyl, ($C_5$-$C_8$)-cycloalkenyl, ($C_6$-$C_{10}$)-bicycloalkyl, and ($C_6$-$C_{10}$)-bicycloalkenyl,
R₃ is selected from the group consisting of hydrogen, halogen, aryl, substituted aryl, heteroaryl, substituted heteroaryl, alkylamino, substitution on alkyl, aryl and heteroaryl with $C_1$-$C_4$-alkyl, halogen, nitro, amino, alkylamino, hydroxyl, alkoxy, carboxyl, ester groups,
wherein alkylamino group is selected from the group consisting of —NH-alkyl, N-dialkyl, NH-cycloalkyl, N-cycloalkyl, or, any alkyl substituted amino derived group derived from either amino acid or heterocycles,
R₄ is selected from the group consisting of hydrogen, alkyl, substituted alkyl, cycloalkyl, acyl, alkanoyl, alkenyl, benzyl, heteroaryl, —CO—CH₂-heteroaryl, —CO-Ph, —CO-substituted aryl, —CO-heteroaryl, or any carbon atom which may be optionally substituted; wherein, alkyl group may be selected from $C_1$-$C_{10}$ carbon chain or branched radical having up to 6 and preferably up to 5 carbon atoms, for example methyl, ethyl, propyl, isopropyl, t-butyl, pentyl, or isopentyl groups, substituted alkyl group is selected from $C_1$-$C_{10}$, containing one or more radical selected from the group consisting of halogen, nitro, amino, hydroxyl, cyano, phenyl, substituted phenyl, carboxyl and an aldehyde
wherein substituted phenyl is selected from the phenyls possessing substitutions at 2 to 5 positions with groups consisting of halogen, hydroxy, ($C_1$-$C_4$)-alkoxy, amino, nitro, cyano, carboxy.

In still another embodiment of the present invention, the structural formula of the representative compounds are having the following formulae:

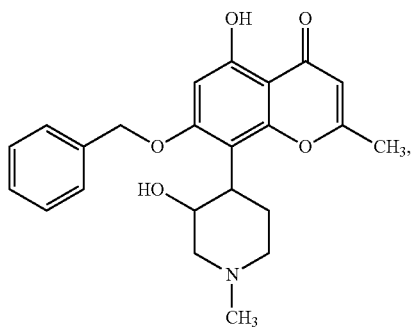

2

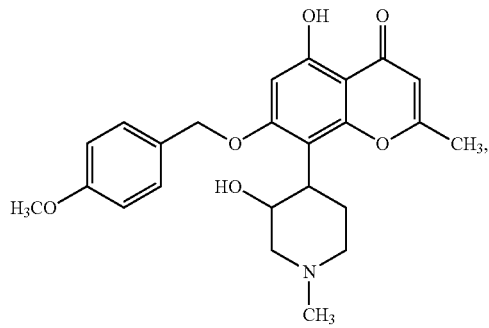

3

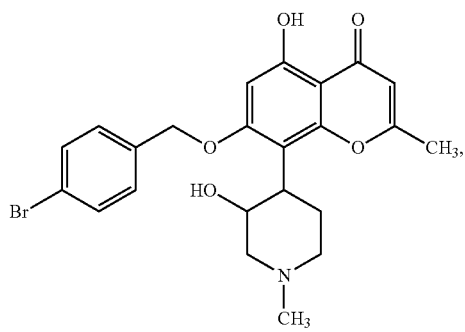

4

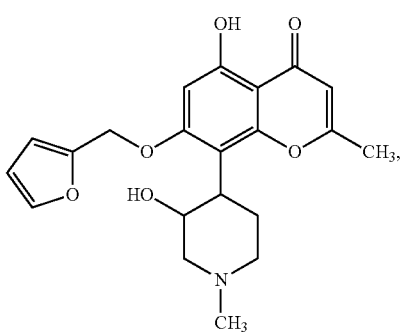

5

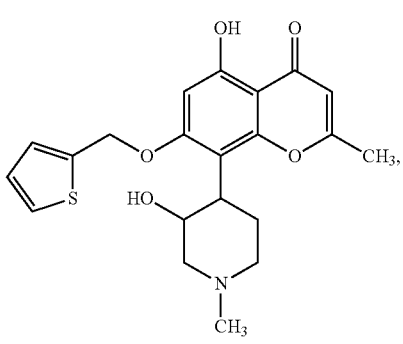

6

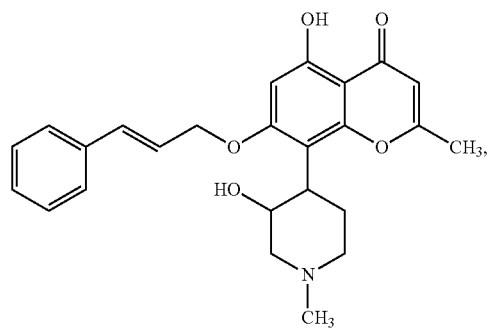

7

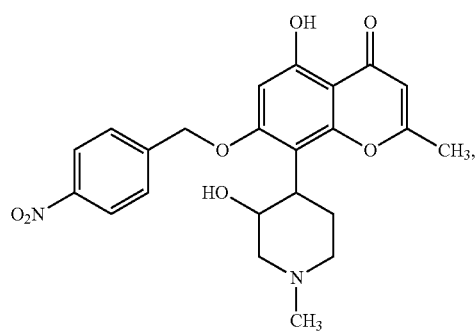
8
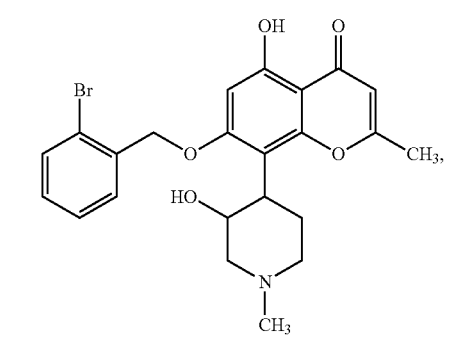
9
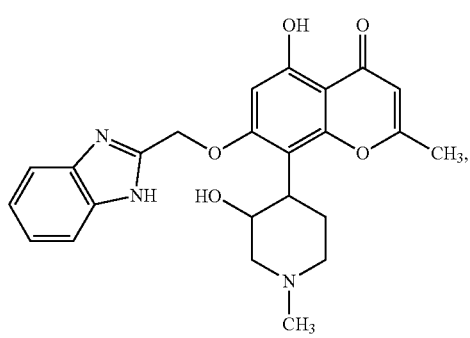
10
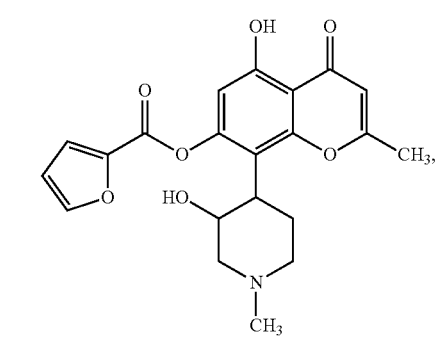
11
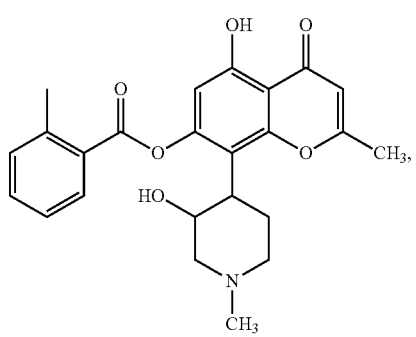
12
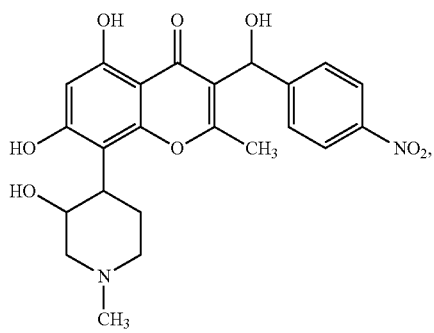
13
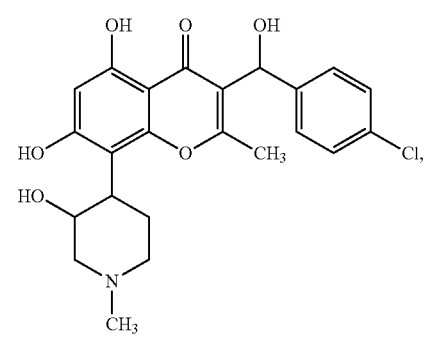
14
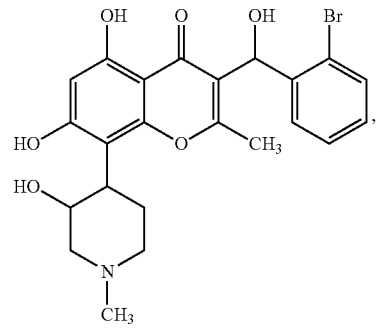
15
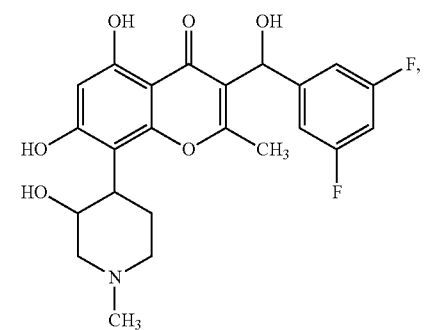
16
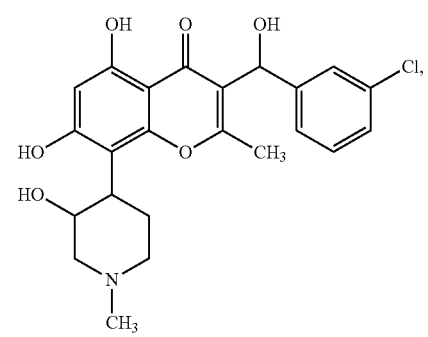
17

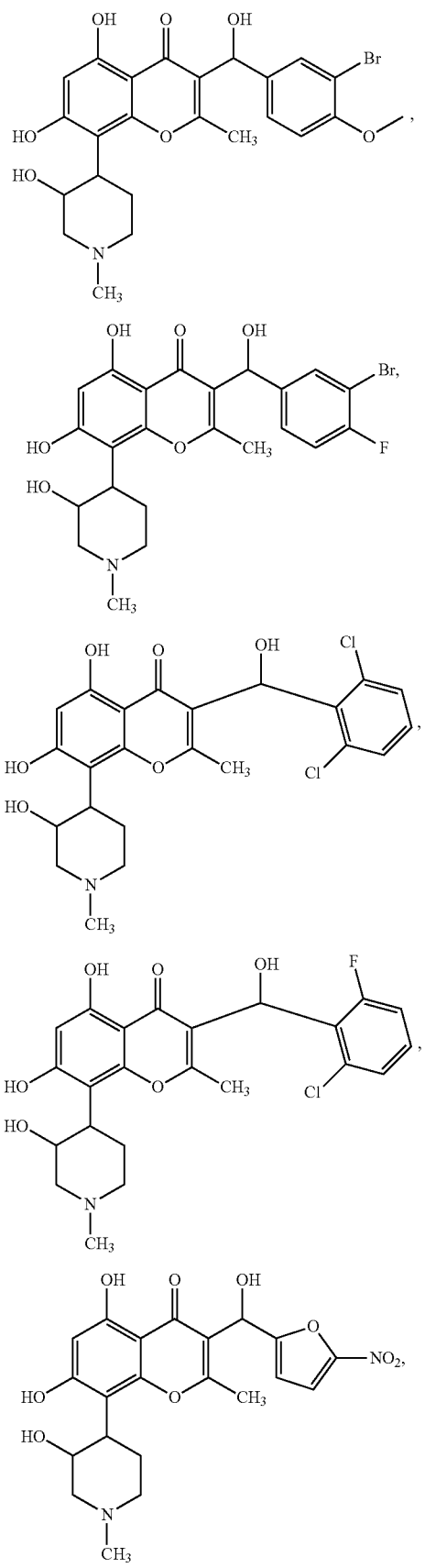
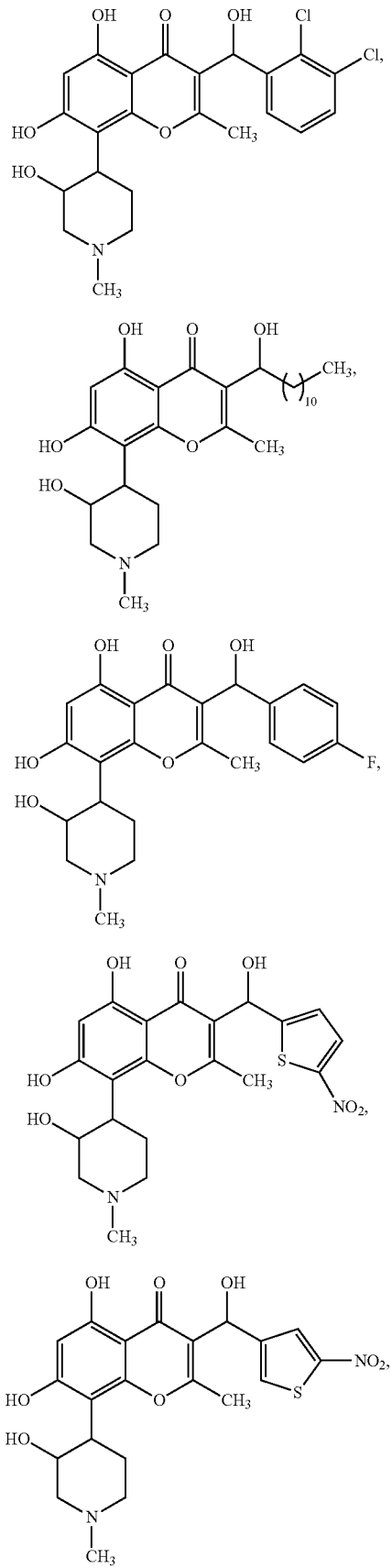

28
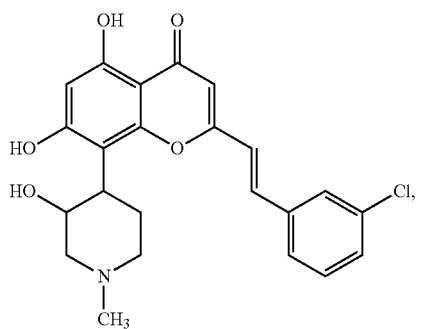
29
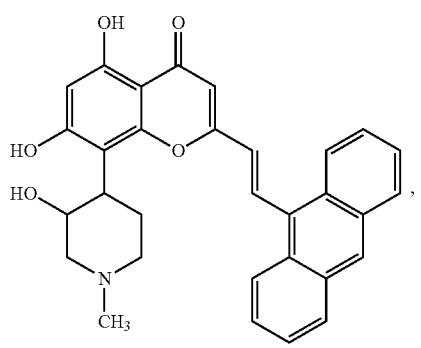
30
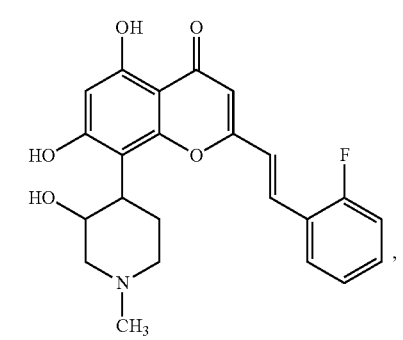
31
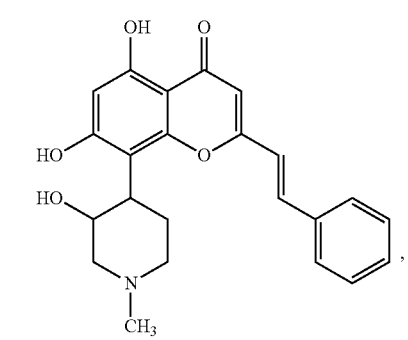
32
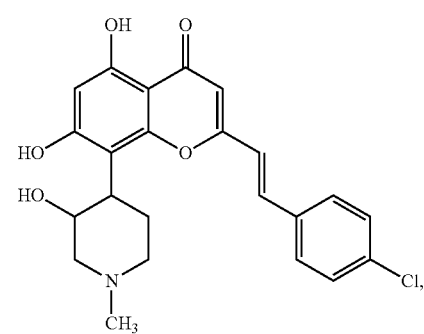
33
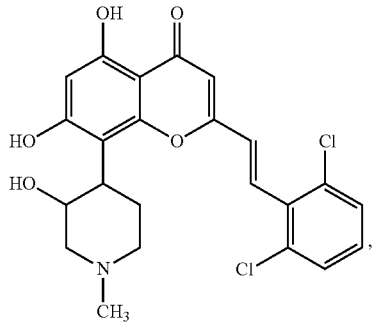
34
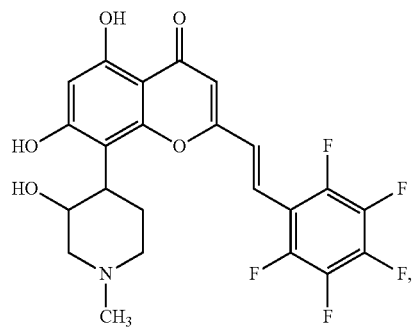
35
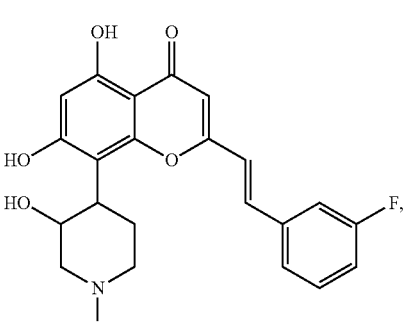
36
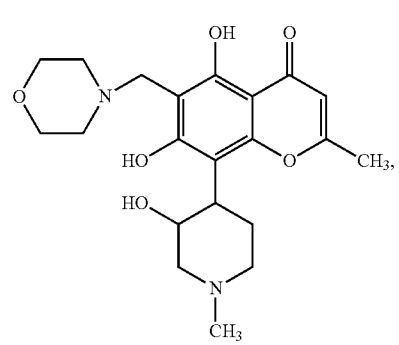
37
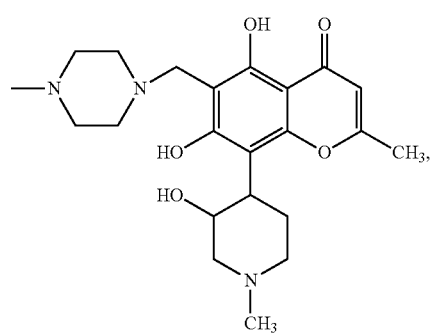

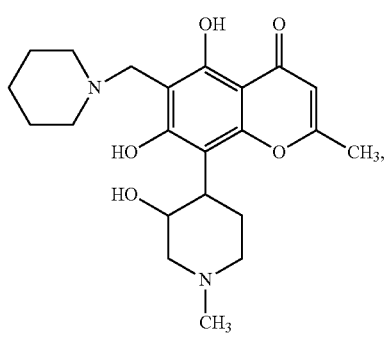

38

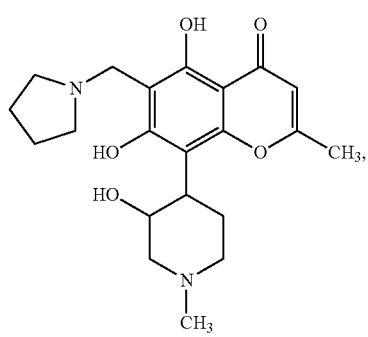

39

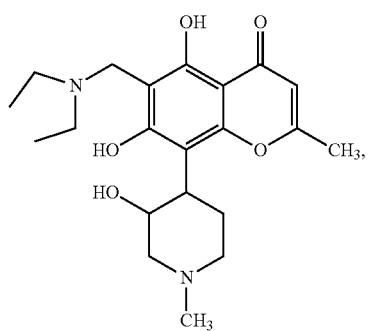

40

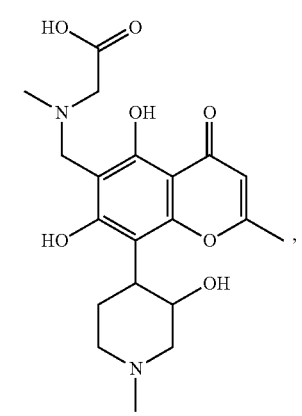

41

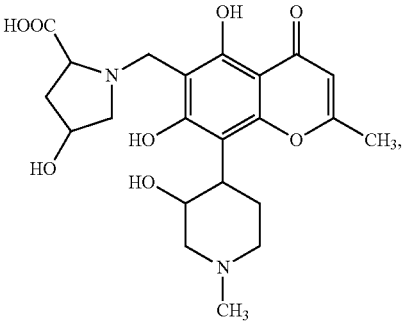

42

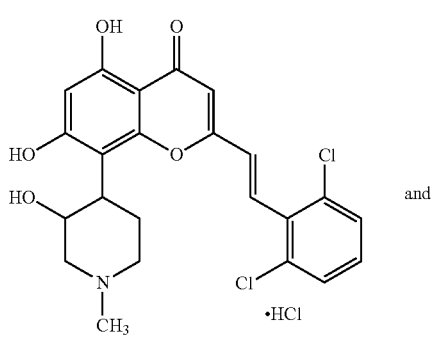

33·HCl and

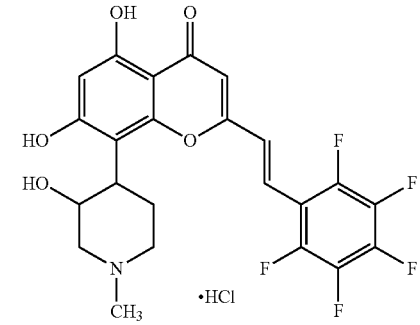

34·HCl

In yet another embodiment of the present invention, the salts of compounds of formula A, are selected from the group consisting of hydrochloride, hydrobromide, and methane sulfonate.

In still another embodiment of the present invention, the compounds exhibit inhibition of cyclin-dependent kinase-2/cyclin A (CDK-2/A) and cyclin-dependent kinase-9/cyclin T1 (CDK-9/T1).

In yet another embodiment of the present invention, the compounds for use in treating or preventing the development of a proliferative disorder selected from the group consisting of breast cancer and leukemia.

In still another embodiment of the present invention, the compounds showed $IC_{50}$ values for CDK-2/A inhibition from 16 nM to 608 nM In yet another embodiment of the present invention, the compounds showed $IC_{50}$ values for CDK-9-T1 inhibition from 2 nM to 30 nM.

In still another embodiment of the present invention, a process for the preparation of compounds of formula A comprising the step of reacting Rohitukine

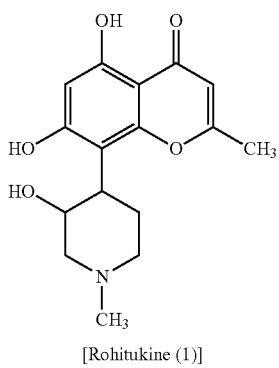 [SMILES: Cc1cc(=O)c2c(O)cc(O)c(C3CCN(C)CC3O)c2o1]

[Rohitukine (1)]

with compound selected from the group consisting of substituted benzyl, substituted benzyl halide, substituted aromatic aldehyde, and substituted aliphatic aldehyde in the presence of base selected from the group consisting of potassium carbonate, 1,4-diazabicyclo[2.2.2]octane (DABCO) and KOH to obtain compound of formula A.

In yet another embodiment of the present invention, the process for the preparation of compound of formula A selected from the group consisting of compound 2 to 12, the process comprising the step of reacting Rohitukine with a compound selected from the group consisting of substituted benzyl, substituted benzyl halide, and aldehyde in the presence of potassium carbonate, for a period from 5 to 15 minutes to obtain compound of formula A selected from the group consisting of compound 2 to 12.

In yet another embodiment of the present invention, the process for the preparation of compound of formula A selected from the group consisting of compound 13 to 27 comprising the step of reacting Rohitukine with a compound selected from the group consisting of substituted aromatic aldehyde and aliphatic aldehyde in the presence of DABCO for a period from 10 to 15 days to obtain compound of formula A selected from the group consisting of compound 13 to 27.

In still another embodiment of the present invention the process for the preparation of compound of formula A selected from the group consisting of compound 28 to 35, comprising the step of reacting Rohitukine with a compound selected from the group consisting of substituted aromatic aldehyde and aliphatic aldehyde in the presence of KOH for a period from 10 to 20 hrs to obtain compound of formula A selected from the group consisting of compound 28 to 35.

In yet another embodiment of the present invention, the process for the preparation of compound of formula A selected from the group consisting of compound 36 to 42 comprising the step of reacting Rohitukine with formaldehyde and a secondary amine selected from the group consisting of morpholine, N-methyl-piperazine, piperidine, pyrrolidine, diethylamine, sarcosin, and 4-hydroxyproline in the presence of a solvent selected from the group consisting of DMSO and methanol:water (7:3) to obtain compound of formula A selected from the group consisting of compound 36 to 42.

BRIEF DESCRIPTION OF ACCOMPANYING DRAWINGS

DETAILED DESCRIPTION OF THE INVENTION

Figure 1:
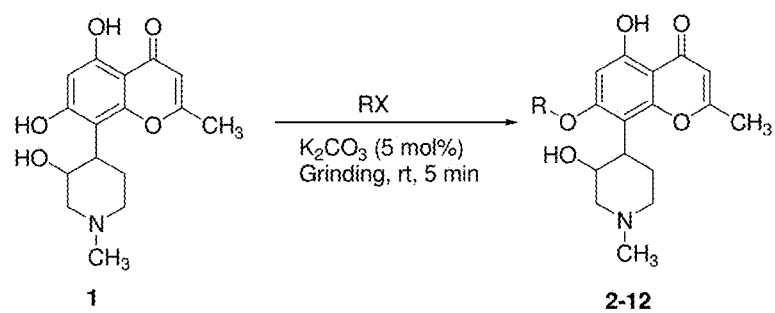
FIG. 1 is a diagram illustrating the chemical synthesis of 5,7-dihydroxy-8-(3-hydroxy-1-methylpiperidin-4-yl)-2-methyl-4H-chromen-4-one compounds 2-12

The present invention provides the Rohitukine analogs of formula A. The present invention further provides the 5,7-dihydroxy-8-(3-hydroxy-1-methylpiperidin-4-yl)-4H-chromen-4-ones (Rohitukine) analogs of formulae I and II and salts thereof, as potent anticancer agents and as inhibitors of cyclin-dependent kinases and the process for the preparation thereof.

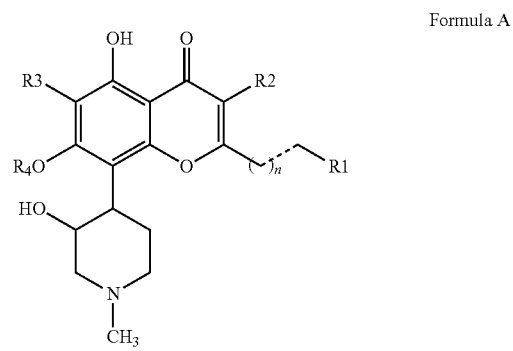

Formula A

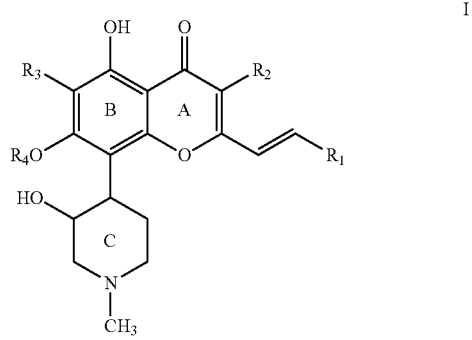

I

-continued

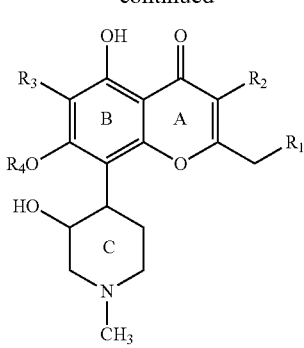

II wherein,
n=0 or 1, when n=1 dotted line indicates the double bond.

R$_1$ is selected from the group consisting of alkyl, substituted alkyl, alkyl having 1 to 6 carbon atoms, aryl, substituted aryl, fused aryl (for example naphthalene and anthracene) heteroaryl, substituted heteroaryl, substitution on alkyl, aryl and heteroaryl with C$_1$-C$_4$-alkyl, halogen, nitro, amino, alkyl substituted amino, hydroxyl, alkoxy, carboxyl, COO-alkyl C$_1$-C$_4$ wherein alkyl is long chain or branched.

R$_2$ is hydrogen or

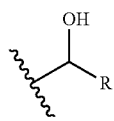

wherein R is selected from the group consisting of alkyl, substituted alkyl, alkyl having 1 to 15 carbon atoms with branched or unbranched, aryl, substituted aryl, fused aryl (for example naphthalene and anthracen), heteroaryl, substituted heteroaryl, substitution on alkyl, aryl and heteroaryl with C$_1$-C$_4$-alkyl, halogen, nitro, amino, alkyl substituted amino, alkyl amino (may be —NH-alkyl, N-dialkyl) hydroxyl, alkoxy, carboxyl, ester groups. Alkyl group is selected from (C$_1$-C$_6$)-alkyl, (C$_1$-C$_4$)-haloalkyl, (C$_1$-C$_4$)-alkoxy, (C$_1$-C$_4$)-haloalkoxy; or is (C$_5$-C$_8$)-cycloalkyl, (C$_5$-C$_8$)-cycloalkenyl, (C$_6$-C$_{10}$)-bicycloalkyl, (C$_6$-C$_{10}$)-bicycloalkenyl.

R$_3$ is selected from the group consisting of hydrogen, halogen, aryl, substituted aryl, heteroaryl, substituted heteroaryl, alkylamino, substitution on alkyl, aryl and heteroaryl with C$_1$-C$_4$-alkyl, halogen, nitro, amino, alkylamino (alkylamino may be —NH-alkyl, N-dialkyl, NH-cycloalkyl, N-cycloalkyl, or, any alkyl substituted amino derived group derived from either amino acid or heterocycles like piperidine or morpholine) hydroxyl, alkoxy, carboxyl, ester groups.

R$_4$ is selected from the group consisting of hydrogen, alkyl, substituted alkyl, cycloalkyl, acyl, alkanoyl, alkenyl, benzyl, heteroaryl, —CO—CH$_2$-heteroaryl, —CO-Ph, —CO-substituted aryl, —CO-heteroaryl, or any carbon atom which may be optionally substituted; wherein, alkyl group may be selected from C$_1$-C$_{10}$ carbon chain or branched radical having up to 6 and preferably up to 5 carbon atoms, for example methyl, ethyl, propyl, isopropyl, t-butyl, pentyl, or isopentyl groups, substituted alkyl group may be selected from C$_1$-C$_{10}$, containing one or more radical selected from the group consisting of halogen, nitro, amino, hydroxyl, cyano, phenyl, substituted phenyl, carboxyl and an aldehyde wherein substituted phenyl group may be selected from the phenyls possessing substitutions at 2-5 positions with groups consisting of halogen, hydroxy, (C$_1$-C$_4$)-alkoxy, amino, nitro, cyano, carboxy and the like.

In one embodiment, the patient is human. In another embodiment, the proliferative disease is cancer.

As used herein, the terms below have the meanings indicated.

The term "acyl," as used herein, alone or in combination, refers to a carbonyl attached to an alkenyl, alkyl, aryl, cycloalkyl, heteroaryl, heterocyclyl, or any other moiety where the atom attached to the carbonyl is carbon. An "acetyl" group refers to a —C(O)CH$_3$ group.

An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds optionally substituted and containing from 2 to 20, preferably 2 to 6, carbon atoms. Alkenyl refers to a carbon-carbon double bond system attached at two or more positions such as ethenylene [(—CH═CH—),(—C::C—)]. Examples of alkenyl radicals include ethenyl, propenyl, 2-methylpropenyl, 1,4-butadienyl and the like.

The term "alkoxy," as used herein, alone or in combination, refers to an alkyl ether radical, optionally substituted wherein the term alkyl is as defined below. Examples of alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical optionally substituted containing from 1 to 20 and including 20, preferably 1 to 10, and more preferably 1 to 6, carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, nonyl and the like.

The term "alkylamino" as used herein, alone or in combination, refers to an alkyl group optionally substituted attached to the parent molecular moiety through an amino group. Alkylamino groups may be mono- or dialkylated, forming groups such as, for example, N-methylamino, N-ethylamino, N,N-dimethylamino, N,N-ethylmethylamino and the like.

The term "alkynyl," as used herein, alone or in combination, refers to a straight-chain or branched chain hydrocarbon radical having one or more triple bonds and containing from 2 to 20, preferably from 2 to 6, more preferably from 2 to 4, carbon atoms. "Alkynyl" refers to a carbon-carbon triple bond attached at two positions such as ethynylene (—C:::C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like.

The term "amino," as used herein, alone or in combination, refers to —NRR', wherein R and R' are independently selected from the group consisting of hydrogen, alkyl, acyl, heteroalkyl, aryl, cycloalkyl, heteroaryl, and heterocycloalkyl, any of which may themselves be optionally substituted.

The term "aryl" as used herein, alone or in combination, means a carbocyclic aromatic system containing one, two or three rings wherein such rings may be attached together in a pendent manner or may be fused optionally substituted with at least one halogen, an alkyl containing from 1 to 3 carbon atoms, an alkoxyl, an aryl radical, a nitro function, a polyether radical, a heteroaryl radical, a benzoyl radical, an alkyl ester group, a carboxylic acid, a hydroxyl optionally protected with an acetyl or benzoyl group, or an amino function optionally protected with an acetyl or benzoyl group or optionally substituted with at least one alkyl containing from 1 to 12 carbon atoms.

The term "arylalkyl" or "aralkyl," as used herein, alone or in combination, refers to an aryl group attached to the parent molecular moiety through an alkyl group.

The terms "benzo" and "benz," as used herein, alone or in combination, refer to the divalent radical $C_6H_4=$ derived from benzene. Examples include benzothiophene and benzimidazole.

The terms "carbamate" and "carbamoyl" as used herein, alone or in combination, refers to an ester of carbamic acid (—NHCOO—) which may be attached to the parent molecular moiety from either the nitrogen or acid end, and which may be optionally substituted as defined herein.

The term "carbonyl," as used herein, when alone includes formyl [—C(O)H] and in combination is a —C(O)— group.

The term "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cycloalkyl," or, alternatively, "carbocycle" as used herein, alone or in combination, refers to a saturated or partially saturated monocyclic, bicyclic or tricyclic alkyl radical wherein each cyclic moiety contains from 3 to 12, preferably five to seven, carbon atom ring members and which may optionally be a benzo-fused ring system which is optionally substituted as defined herein. Examples of such cycloalkyl radicals include cyclopropyl, cyclobutyl, cyclopentyl, cyclohexyl, cycloheptyl, octahydronaphthyl, 2,3-dihydro-1H-indenyl, adamantyl and the like. "Bicyclic" and "tricyclic" as used herein are intended to include both fused ring systems, such as decahydronapthalene, octahydronapthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxygen atom bridging two moieties linked at carbon atoms.

The term "halo," or "halogen," as used herein, alone or in combination, refers to fluorine, chlorine, bromine, or iodine.

The term "haloalkyl" as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CHF—), difluoromethylene (—CF$_2$—), chloromethylene (—CHCl—) and the like.

The term "heteroaryl" as used herein, alone or in combination, refers to 3 to 7 membered, preferably 5 to 7-membered, unsaturated heteromonocyclic rings, or fused polycyclic rings in which at least one of the fused rings is unsaturated, wherein at least one atom is selected from the group consisting of O, S, and N. The term also embraces fused polycyclic groups wherein heterocyclic radicals are fused with aryl radicals, wherein heteroaryl radicals are fused with other heteroaryl radicals, or wherein heteroaryl radicals are fused with cycloalkyl radicals. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groupsincludecarbazolyl, benzidolyl, phenanthrolinyl, dibenzofuranyl, acridinyl, phenanthridinyl, xanthenyl and the like.

The terms "heterocycloalkyl" and, interchangeably, "heterocyclyl" as used herein, alone or in combination, each refer to a saturated, partially unsaturated, or fully unsaturated monocyclic, bicyclic, or tricyclic heterocyclic radical containing at least one, preferably 1 to 4, and more preferably 1 to 2 heteroatoms as ring members, wherein each said heteroatom may be independently selected from the group consisting of nitrogen, oxygen, and sulfur, and wherein there are preferably 3 to 8 ring members in each ring, more preferably 3 to 7 ring members in each ring, and most preferably 5 to 6 ring members in each ring. "Heterocycloalkyl" and "heterocyclyl" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Heterocyclyl groups of the invention are exemplified by aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihydropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocyclyl groups may be optionally substituted unless specifically prohibited.

The term "hydroxy" as used herein, alone or in combination, refers to —OH.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

Asymmetric centers exist in the compounds of the present invention. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds of the present invention may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

Optical isomers are compounds with the same molecular formula but differ in the way they rotate plane polarized light. There are two types of optical isomers. The first type of optical isomers are compounds that are mirror images of one another but cannot be superimposed on each other. These isomers are called "enantiomers." The second type of optical isomers are molecules that are not mirror images but each molecule rotates plane polarized light and are considered optically-active. Such molecules are called "diastereoisomers." Diastereoisomers differ not only in the way they rotate plane polarized light, but also their physical properties. The term "optical isomer" comprises more particularly the enantiomers and the diastereoisomers, in pure form or in the form of a mixture.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

In a second aspect of the invention, a method is presented for treating or preventing cancer diseases such as leukemia, breast cancer etc. by identifying a patient suffering from or at a risk of developing a proliferative disease and administering to the patient a therapeutically-effective amount of a compound represented by the formulae I and II, Compounds of the invention derived from Formulae I and II include, but are not limited to, the following chemical structures:

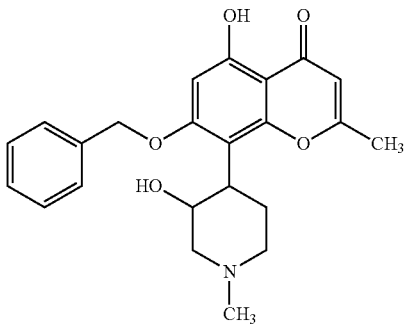 [SMILES: Cc1cc(=O)c2c(O)cc(OCc3ccccc3)c(C3CCN(C)CC3O)c2o1]

7-(Benzyloxy)-5-hydroxy-8-(3-hydroxy-1-methylpiperidin-4-yl)-2-methyl-4H-2

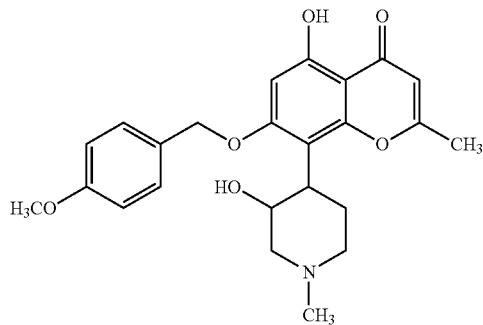 [SMILES: COc1ccc(COc2cc(O)c3c(=O)cc(C)oc3c2C2CCN(C)CC2O)cc1]

7-(4-Methoxybenzyloxy)-5-hydroxy-8-(3-hydroxy-1-methylpiperidin-4-yl)-2-methyl-4H-chromen-4-one; 3

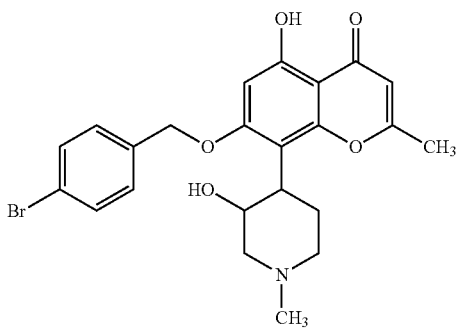 [SMILES: Cc1cc(=O)c2c(O)cc(OCc3ccc(Br)cc3)c(C3CCN(C)CC3O)c2o1]

7-(4-Bromobenzyloxy)-5-hydroxy-8-(3-hydroxy-1-methylpiperidin-4-yl)-2-methyl-4H-chromen-4-one; 4

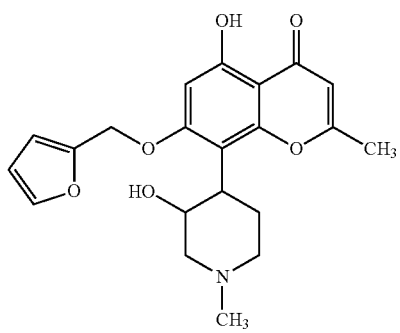

7-((Furan-2-yl)methoxy)-5-hydroxy-8-(3-hydroxy-1-methylpiperidin-4-yl)-2-methyl-4H-chromen-4-one; 5

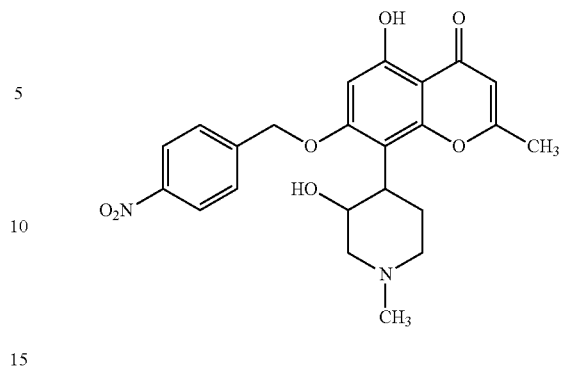

7-(4-Nitrobenzyloxy)-5-hydroxy-8-(3-hydroxy-1-methylpiperidin-4-yl)-2-methyl-4H-chromen-4-one; 8

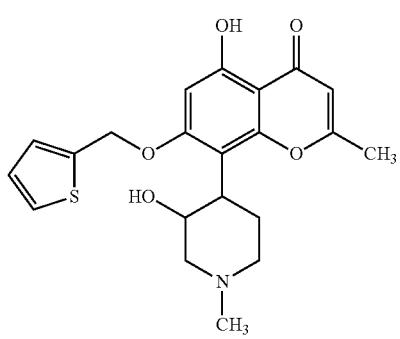 [SMILES: Cc1cc(=O)c2c(O)cc(OCc3cccs3)c(C3CCN(C)CC3O)c2o1]

7-((Thiophen-2-yl)methoxy)-5-hydroxy-8-(3-hydroxy-1-methylpiperidin-4-yl)-2-methyl-4H-chromen-4-one; 6

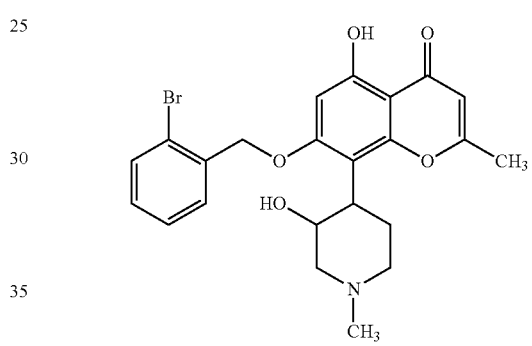

7-(2-Bromobenzyloxy)-5-hydroxy-8-(3-hydroxy-1-methylpipetidin-4-yl)-2-methyl-4H-chromen-4-one; 9

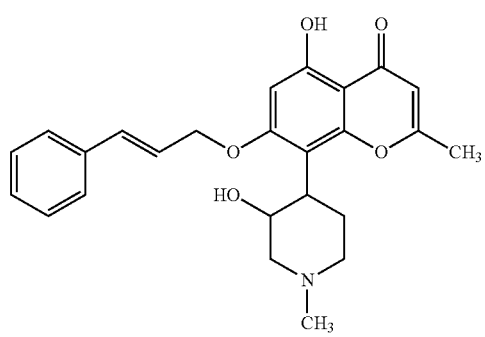 [SMILES: Cc1cc(=O)c2c(O)cc(OC/C=C/c3ccccc3)c(C3CCN(C)CC3O)c2o1]

7-(Cinnamyloxy)-5-hydroxy-8-(3-hydroxy-1-methylpiperidin-4-yl)-2-methyl-4H-chromen-4-one; 7

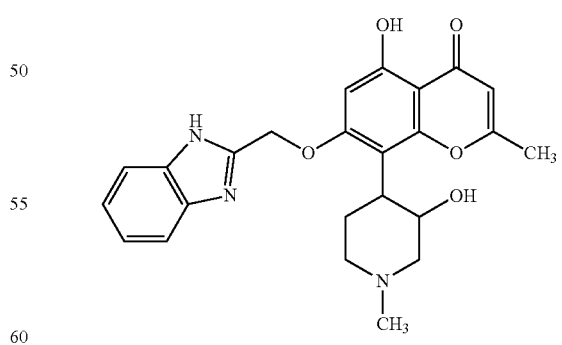

7-((1H-Benzo[d]imidazol-2-yl)methoxy)-5-hydroxy-8-(3-hydroxy-1-methylpiperidin-4-yl)-2-methyl-4H-chromen-4-one; 10

25

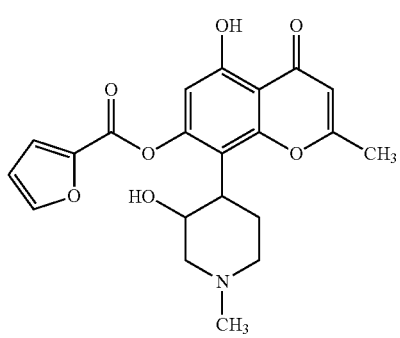 [SMILES: Cc1cc(=O)c2c(O)cc(OC(=O)c3ccco3)c(C3CCN(C)CC3O)c2o1]

5-Hydroxy-8-(3-hydroxy-1-methylpiperidin-4-yl)-2-methyl-4-oxo-4H-chromen-7-yl furan-2-carboxylate; 11

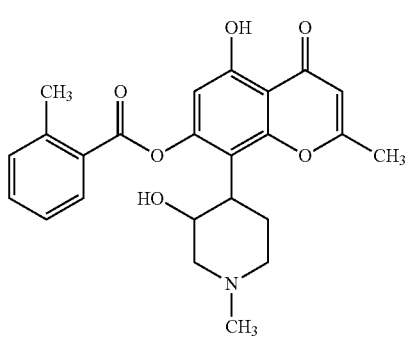 [SMILES: Cc1cc(=O)c2c(O)cc(OC(=O)c3ccccc3C)c(C3CCN(C)CC3O)c2o1]

5-Hydroxy-8-(3-hydroxy-1-methylpiperidin-4-yl)-2-methyl-4-oxo-4H-chromen-7-yl 2-methylbenzoate; 12

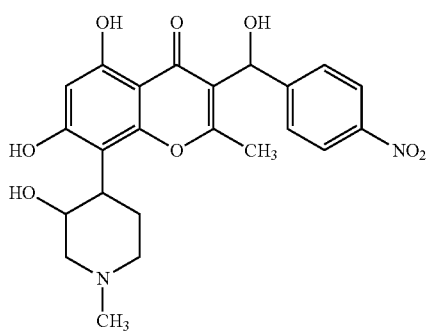 [SMILES: Cc1oc2c(C3CCN(C)CC3O)c(O)cc(O)c2c(=O)c1C(O)c1ccc([N+](=O)[O-])cc1]

5,7-Dihydroxy-3-(hydroxy(4-nitrophenyl)methyl)-8-(3-hydroxy-1-methylpiperidin-4-yl)-2-methyl-4H-chromen-4-one; 13

26

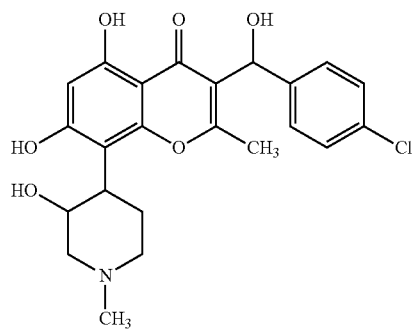 [SMILES: Cc1oc2c(C3CCN(C)CC3O)c(O)cc(O)c2c(=O)c1C(O)c1ccc(Cl)cc1]

3-((4-Chlorophenyl)(hydroxy)methyl)-5,7-dihydroxy-8-(3-hydroxy-1-methylpiperidin-4-yl)-2-methyl-4H-chromen-4-one; 14

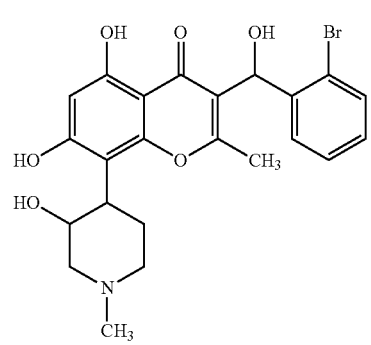 [SMILES: Cc1oc2c(C3CCN(C)CC3O)c(O)cc(O)c2c(=O)c1C(O)c1ccccc1Br]

3-((2-Bromophenyl)(hydroxy)methyl)-5,7-dihydroxy-8-(3-hydroxy-1-methylpiperidin-4-yl)-2-methyl-4H-chromen-4-one; 15

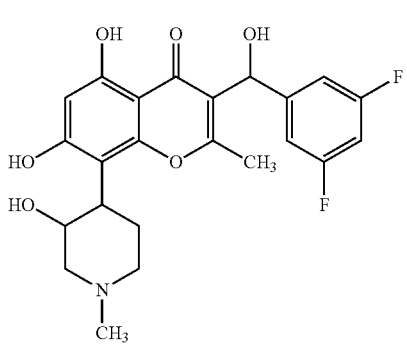 [SMILES: Cc1oc2c(C3CCN(C)CC3O)c(O)cc(O)c2c(=O)c1C(O)c1cc(F)cc(F)c1]

3-((3,5-Difluorophenyl)(hydroxy)methyl)-5,7-dihydroxy-8-(3-hydroxy-1-methylpiperidin-4-yl)-2-methyl-4H-chromen-4-one; 16

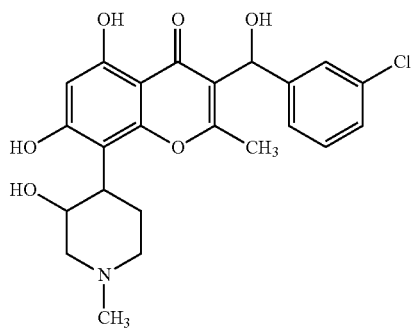 [SMILES: Cc1oc2c(C3CCN(C)CC3O)c(O)cc(O)c2c(=O)c1C(O)c1cccc(Cl)c1]

3-((3-Chlorophenyl)(hydroxy)methyl)-5,7-dihydroxy-8-(3-hydroxy-1-methylpiperidin-4-yl)-2-methyl-4H-chromen-4-one; 17

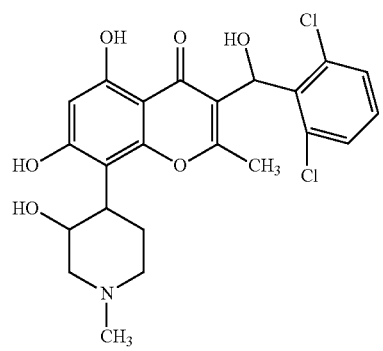

3-(2,6-Dichlorophenyl)(hydroxy)methyl)-5,7-dihydroxy-8-(3-hydroxy-1-methylpiperidin-4-yl)-2-methyl-4H-chromen-4-one; 20

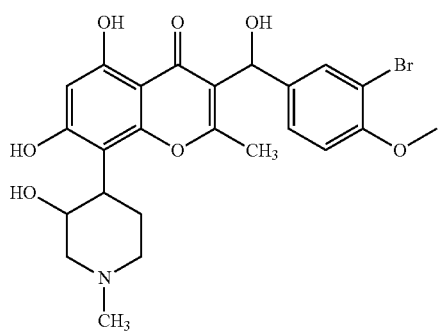 [SMILES: COc1ccc(C(O)c2c(C)oc3c(C4CCN(C)CC4O)c(O)cc(O)c3c2=O)cc1Br]

3-((3-Bromo-4-methoxyphenyl)(hydroxy)methyl)-5,7-dihydroxy-8-(3-hydroxy-1-methylpiperidin-4-yl)-2-methyl-4H-chromen-4-one; 18

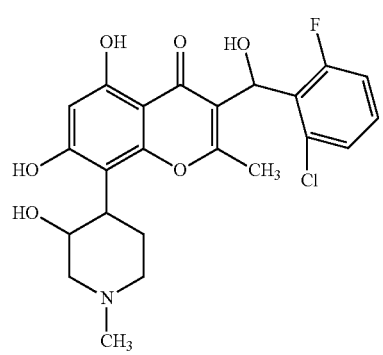

3-((2-Chloro-6-fluorophenyl)(hydroxy)methyl)-5,7-dihydroxy-8-(3-hydroxy-1-methylpiperidin-4-yl)-2-methyl-4H-chromen-4-one; 21

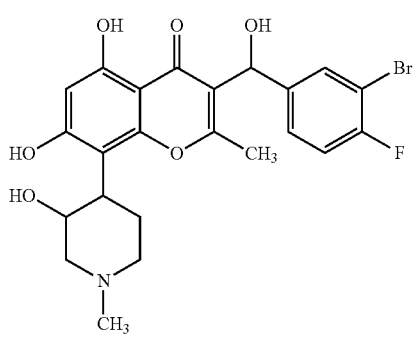 [SMILES: Cc1oc2c(C3CCN(C)CC3O)c(O)cc(O)c2c(=O)c1C(O)c1ccc(F)c(Br)c1]

3-((3-Bromo-4-fluorophenyl)(hydroxy)methyl)-5,7-dihydroxy-8-(3-hydroxy-1-methylpiperidin-4-yl)-2-methyl-4H-chromen-4-one; 19

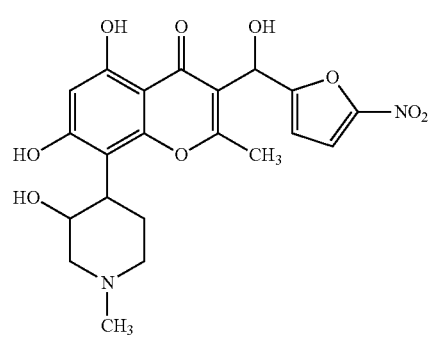 [SMILES: Cc1oc2c(C3CCN(C)CC3O)c(O)cc(O)c2c(=O)c1C(O)c1ccc([N+](=O)[O-])o1]

5,7-Dihydroxy-3-(hydroxy(5-nitrofuran-2-yl)methyl)-8-(3-hydroxy-1-methylpiperidin-4-yl)-2-methyl-4H-chromen-4-one; 22

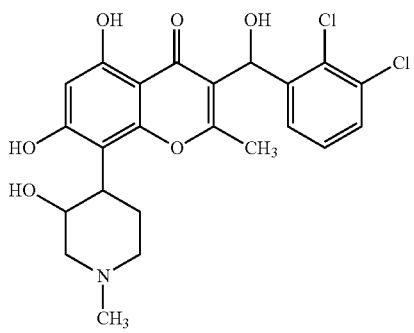 [SMILES: Cc1oc2c(C3CCN(C)CC3O)c(O)cc(O)c2c(=O)c1C(O)c1cccc(Cl)c1Cl]

3-((2,3-Dichlorophenyl)(hydroxy)methyl)-5,7-dihydroxy-8-(3-hydroxy-1-methylpiperidin-4-yl)-2-methyl-4H-chromen-4-one; 23

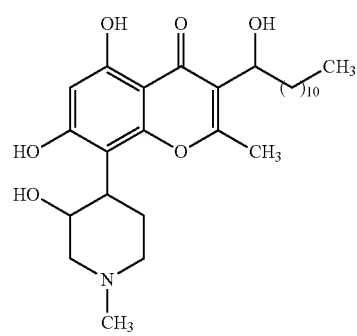

5,7-Dihydroxy-8-(3-hydroxy-1-methylpiperidin-4-yl)-3-(1-hydroxydodecyl)-2-methyl-4H-chromen-4-one; 24

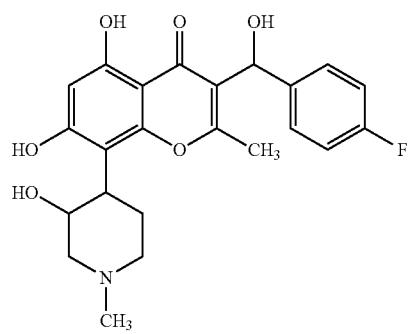 [SMILES: Cc1oc2c(C3CCN(C)CC3O)c(O)cc(O)c2c(=O)c1C(O)c1ccc(F)cc1]

3-((4-Fluorophenyl)(hydroxy)methyl)-5,7-dihydroxy-8-(3-hydroxy-1-methylpiperidin-4-yl)-2-methyl-4H-chromen-4-one; 25

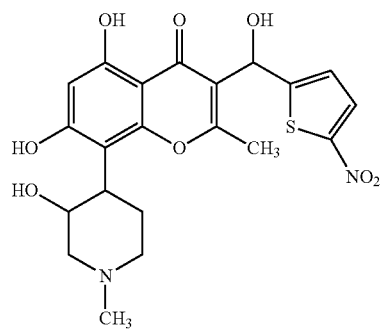 [SMILES: Cc1oc2c(C3CCN(C)CC3O)c(O)cc(O)c2c(=O)c1C(O)c1ccc([N+](=O)[O-])s1]

5,7-Dihydroxy-3-(hydroxy(5-nitrothiophen-2-yl)methyl)-8-(3-hydroxy-1-methylpiperidin-4-yl)-2 methyl-4H-chromen-4-one; 26

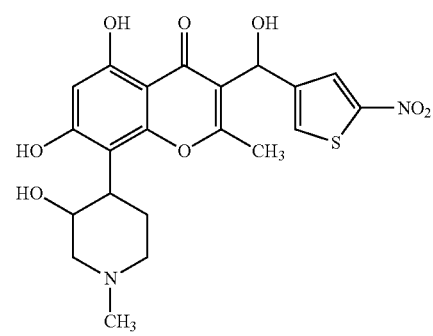 [SMILES: Cc1oc2c(C3CCN(C)CC3O)c(O)cc(O)c2c(=O)c1C(O)c1csc([N+](=O)[O-])c1]

5,7-Dihydroxy-3-(hydroxy(5-nitrothiophen-3-yl)methyl)-8-(3-hydroxy-1-methylpiperidin-4-yl)-2-methyl-4H-chromen-4-one; 27

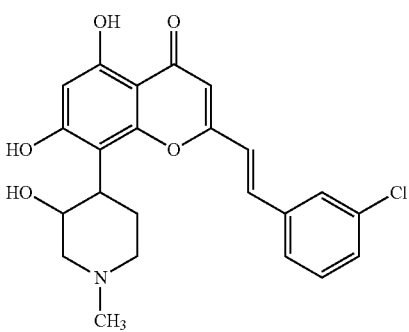 [SMILES: CN1CCC(c2c(O)cc(O)c3c(=O)cc(/C=C/c4cccc(Cl)c4)oc23)C(O)C1]

2-(3-Chlorostyryl)-5,7-dihydroxy-8-(3-hydroxy-1-methyl-piperidin-4-yl)-4H-chromen-4-one; 28

31                                          32

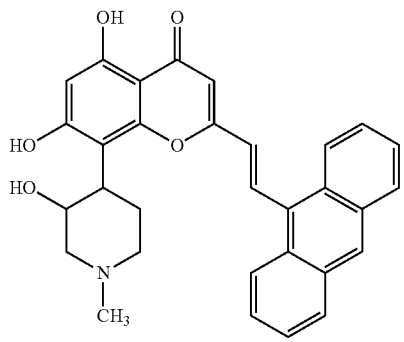 [SMILES: CN1CCC(c2c(O)cc(O)c3c(=O)cc(/C=C/c4c5ccccc5cc5ccccc45)oc23)C(O)C1]

2-((E)-2-(Anthracen-10-yl)vinyl)-5,7-dihydroxy-8-(3-hydroxy-1-methylpiperidin-4-yl)-4H-chromen-4-one; 29

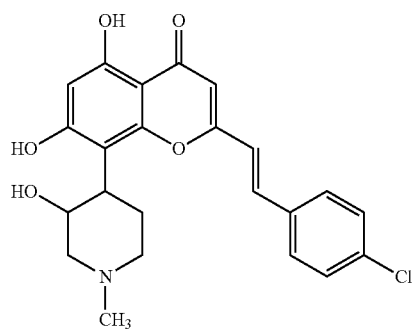

2-(4-Chlorostyryl)-5,7-dihydroxy-8-(3-hydroxy-1-methylpiperidin-4-yl)-4H-chromen-4-one; 32

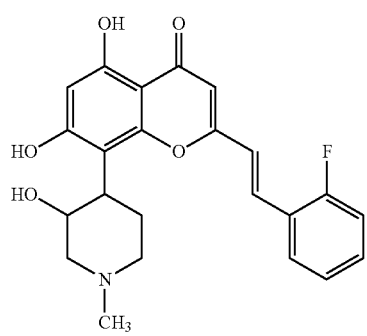 [SMILES: CN1CCC(c2c(O)cc(O)c3c(=O)cc(/C=C/c4ccccc4F)oc23)C(O)C1]

2-(2-Fluorostyryl)-5,7-dihydroxy-8-(3-hydroxy-1-methylpiperidin-4-yl)-4H-chromen-4-one; 30

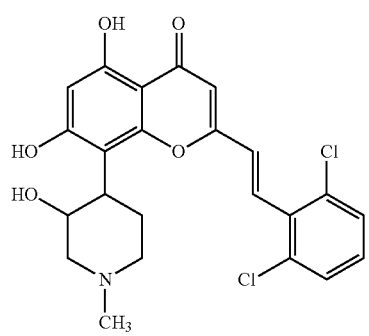

2-(2,3,4,5,6-Pentafluorostyryl)-5,7-dihydroxy-8-(3-hydroxy-1-methylpiperidin-4-yl)-4H-chromen-4-one; 33

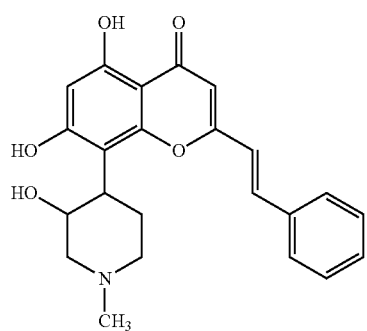 [SMILES: CN1CCC(c2c(O)cc(O)c3c(=O)cc(/C=C/c4ccccc4)oc23)C(O)C1]

2-(4-chlorostyryl)-5,7-dihydroxy-8-(3-hydroxy-1-methylpiperidin-4-yl)-4H-chromen-4-one; 31

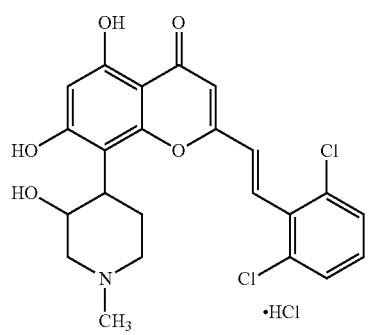 [SMILES: CN1CCC(c2c(O)cc(O)c3c(=O)cc(/C=C/c4c(Cl)cccc4Cl)oc23)C(O)C1 ; Cl]

2-(2,6-dichlorostyryl)-5,7-dihydroxy-8-(3-hydroxy-1-methylpiperidin-4-yl)-4H-chromen-4-one hydrochloride; 33

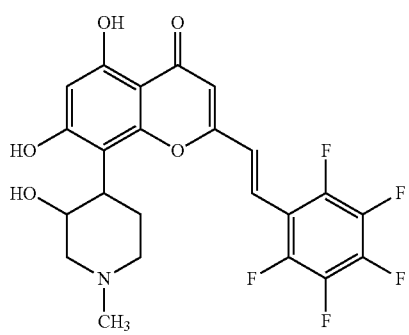 [SMILES: CN1CCC(c2c(O)cc(O)c3c(=O)cc(/C=C/c4c(F)c(F)c(F)c(F)c4F)oc23)C(O)C1]

2-(3-fluorostyryl)-5,7-dihydroxy-8-(3-hydroxy-1-methylpi-
peridin-4-yl)-4H-chromen-4-one; 34

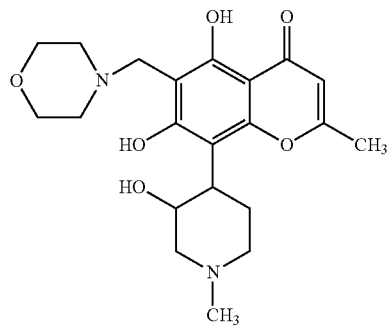

5,7-Dihydroxy-8-(3-hydroxy-1-methylpiperidin-4-yl)-2-
methyl-6-((4-methylpiperazin-1-yl)methyl)-4H-
chromen-4-one; 36

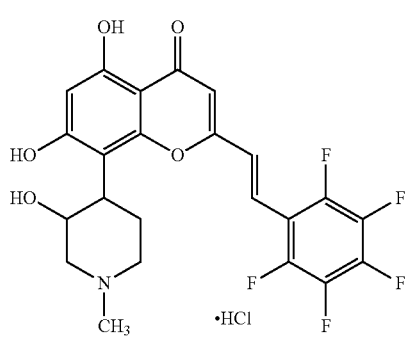 [SMILES: CN1CCC(c2c(O)cc(O)c3c(=O)cc(/C=C/c4c(F)c(F)c(F)c(F)c4F)oc23)C(O)C1 ; Cl]

2-(2,3,4,5,6-pentafluorostyryl)-5,7-dihydroxy-8-(3-hy-
droxy-1-methylpiperidin-4-yl)-4H-chromen-4-one
hydrochloride; 34.HCl

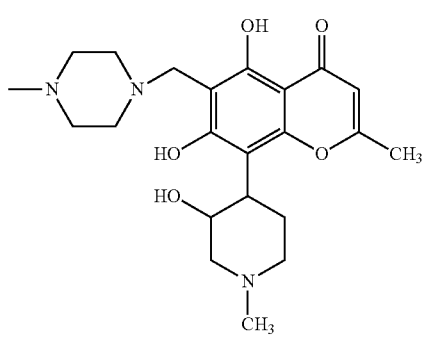

5,7-dihydroxy-8-(3-hydroxy-1-methylpiperidin-4-yl)-2-
methyl-6-((piperidin-1-yl)methyl)-4H-chromen-4-one;
37

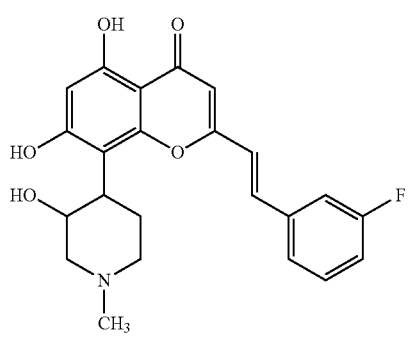 [SMILES: CN1CCC(c2c(O)cc(O)c3c(=O)cc(/C=C/c4cccc(F)c4)oc23)C(O)C1]

5,7-Dihydroxy-8-(3-hydroxy-1-methylpiperidin-4-yl)-2-
methyl-6-(morpholinomethyl)-4H-chromen-4-one; 35

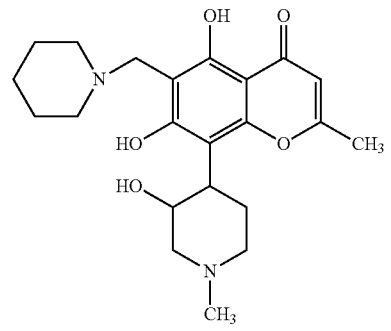 [SMILES: Cc1cc(=O)c2c(O)c(CN3CCCCC3)c(O)c(C3CCN(C)CC3O)c2o1]

5,7-dihydroxy-8-(3-hydroxy-1-methylpiperidin-4-yl)-2-
methyl-6-((pyrrolidin-1-yl)methyl)-4H-chromen-4-one;
38

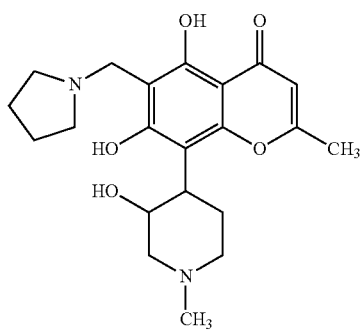 [SMILES: Cc1cc(=O)c2c(O)c(CN3CCCC3)c(O)c(C3CCN(C)CC3O)c2o1]

6-((Diethylamino)methyl)-5,7-dihydroxy-8-(3-hydroxy-1-methylpiperidin-4-yl)-2-methyl-4H-chromen-4-one; 39

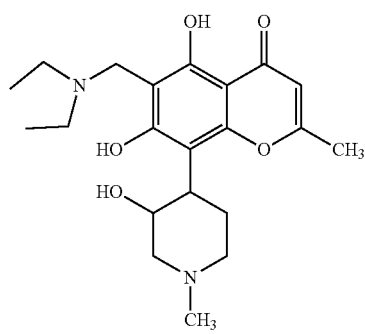 [SMILES: CCN(CC)Cc1c(O)c(C2CCN(C)CC2O)c2oc(C)cc(=O)c2c1O]

2-(N-((5,7-Dihydroxy-8-(3-hydroxy-1-methylpiperidin-4-yl)-2-methyl-4-oxo-4H-chromen-6-yl)methyl)-N-methylamino)acetic acid; 40

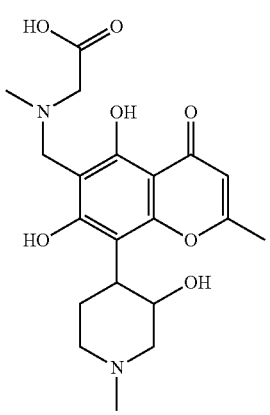

4-hydroxy-1-((5,7-dihydroxy-8-(3-hydroxy-1-methylpiperidin-4-yl)-2-methyl-4-oxo-4H-chromen-6-yl)methyl)pyrrolidine-2-carboxylic acid; 41

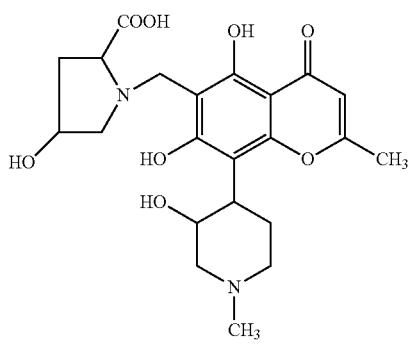 [SMILES: Cc1cc(=O)c2c(O)c(CN3CC(O)CC3C(=O)O)c(O)c(C3CCN(C)CC3O)c2o1]

4-hydroxy-1-((5,7-dihydroxy-8-(3-hydroxy-1-methylpiperidin-4-yl)-2-methyl-4-oxo-4H-chromen-6-yl)methyl)pyrrolidine-2-carboxylic acid; 42

One or more compounds of the invention can be used to treat a patient (e.g. a human) at a risk of developing or already suffering from a proliferative disease, such as breast cancer, leukemia etc.

Methods of Prevention and Treatment.

The compounds of the invention can be used to treat a patient (e.g. a human) that suffers from or is at a risk of suffering from a disease, disorder, condition, or symptom described herein. The compounds of the invention can be used alone or in combination with other agents and compounds in methods of treating or preventing proliferative disease such as cancer. Each such treatment described above includes the step of administering to a patient in need thereof a therapeutically effective amount of the compound of the invention described herein to delay, reduce or prevent such a disease, disorder, condition, or symptom.

Besides being useful for human treatment, the compounds of the present invention are also useful for the treatment of animals, e.g., the veterinary treatment of domesticated animal, companion animals (e.g., dogs and cats), exotic animals, farm animals (e.g., ungulates, including horses, cows, sheep, goats, and pigs), and animals used in scientific research (e.g., rodents).

It is understood that the foregoing examples are merely illustrative of the present invention. Certain modifications of the articles and/or methods employed may be made and still achieve the objectives of the invention. Such modifications are contemplated as within the scope of the claimed invention.

EXAMPLES

The following examples are given by way of illustrating the present invention and should not be construed to limit the scope of present invention Example 1

Isolation of Rohitukine (1) from *Dysoxylum Binectariferum*

To isolate rohitukine, the stem bark of *Dysoxylum binectariferum* (Roxb.) Hook was collected from Western Ghats India. Bark of *Dysoxylum binectariferum* (1.5 kg) was extracted by ethanol (3 L in each cycle) three times and concentrated over rotary evaporator to get crude (110 g, extractive value 7.3%) material. Half of the crude extract (55 g) was again suspended in water (150 ml) and pH was adjusted to 5 by HCl and placed over night (exact period) at room temperature (exact temperature). Then, it was filtered with celite and a clear solution was neutralized with liquid ammonia to get pH 11. The solution was adjusted to 2 L with water and passed through HP20 resin (100 ml, bed size 10% of final volume). Adsorbed material was eluted with increasing proportion of methanol in water, wherein the rohitukine (1) was isolated at 40% methanol in water. Purification was done by crystallization with water-acetone mixture (40:60). Finally 17 g of rohitukine (2.26%) was isolated with >98.5% purity. The compound was characterized by comparison of spectral data with literature values (Naik, R. G. et. al. *Tetrahedron* 1988, 44, 2081). Rohitukine (1): Light yellow crystalline powder; melting point 229-232° C.; $^1$H-NMR (CD$_3$OD, 500 MHz): δ 6.26 (s, 1H, H-6), 6.10 (s, 1H, H-3), 4.22 (brs, 1H, H-3'), 3.82-3.21 (m, 6H of piperidine ring), 2.90 (s, 3H), 2.41 (s, 3H), 1.84 (m, 1H, H-5'a); $^{13}$C NMR (CD$_3$OD+Pyridin-d$_5$, 100 MHz): δ 182.90, 178.24, 166.77, 161.44, 156.96, 108.53, 108.03, 102.73, 69.30, 62.20, 56.60, 44.81, 37.35, 24.03, 23.62, 19.97; ESI-MS: m/z 306.0957 [M+H]$^+$; IR (KBr): ν$_{max}$ 3399, 2924, 2350, 1659, 1556, 1417, 1271, 1186, 841, 757, 554 cm$^{-1}$.

General Procedure for the Synthesis of Ether or Ester Analogs 2-12 of Rohitukine Example 2

Synthesis of ether analog 7-(benzyloxy)-5-hydroxy-8-(3-hydroxy-1-methylpiperidin-4-yl)-2-methyl-4H-chromen-4-one (2)

A general synthetic strategy for compounds 2-12 proposed in present invention is depicted in FIG. 1, Rohitukine (1, 30 mg, 1 mmol) was mixed with equivalent amount of potassium carbonate in a pestle and substituted benzyl or benzyl halide (1.5 equiv) was added to the pestle and triturated intermittently for 5-15 min until reaction gets completed. Reaction mixture was suspended in water and extracted with ethyl acetate. Organic layer was concentrated and purified by preparative TLC in chloroform-methanol (85:15). Light yellow powder; $^1$H NMR (CD$_3$OD, 400 MHz): δ 7.156 (m, 5H, ArH), 6.64 (s, 1H, H-6), 6.126 (s, 1H, H-3), 5.22 (brs, 2H), 4.294 (brs, 1H, H-3'), 3.797-3.453 (m, 6H of piperidine), 2.99 (s, 3H), 2.47 (s, 3H) 1.96 (m, 1H); ESI-MS: m/z 396.2103 [M+H]$^+$; IR (KBr) ν$_{max}$ 3325, 2923, 1658, 1588, 1420, 1270, 1120, 1028, 749 cm$^{-1}$.

Synthesis of ether analog 7-(4-methoxybenzyloxy)-5-hydroxy-8-(3-hydroxy-1-methylpiperidin-4-yl)-2-methyl-4H-chromen-4-one (3)

This compound was synthesized using the similar procedure as described in example 2. White powder; m.p. 208-210° C.; $^1$H NMR (400 MHz, D$_2$O, ppm): δ 12.39 (s, 1H, H-bonded), 7.71 (d, J=8.2 Hz, 2H), 7.09 (d, J=8.2 Hz, 2H), 5.82 (s, 1H), 5.57 (s, 1H), 5.29 (d, J=12.7 Hz, 1H), 4.71 (d, J=12.7 Hz, 1H), 4.15 (brs, 1H), 3.80 (s, 3H), 3.57-3.35 (m, 6H of piperidine), 2.83 (s, 3H), 2.27 (s, 3H), 1.54 (m, 1H); $^{13}$C NMR (100 MHz, CD$_3$OD, ppm): δ 179.62, 176.46, 163.71, 159.99, 159.69, 155.30, 134.37, 120.21, 113.72, 106.80, 106.12, 102.14, 98.04, 68.37, 62.58, 62.27, 61.80, 54.84, 51.53, 35.55, 19.85, 19.38; IR (KBr): ν$_{max}$ 3415, 2854, 1617, 1352, 1258, 1180 cm$^{-1}$; ESI-MS: m/z 448.20 [M+Na]$^+$.

Synthesis of ether analog 7-(4-Bromobenzyloxy)-5-hydroxy-8-(3-hydroxy-1-methylpiperidin-4-yl)-2-methyl-4H-chromen-4-one (4)

This compound was synthesized using the similar procedure as described in example 2. Off-white powder; m.p. 248-250° C.; 1H NMR (400 MHz, CD$_3$OD, ppm): δ 7.68 (m, 4H), 5.97 (s, 1H), 5.37 (s, 1H), 5.33 (d, J=12 Hz, 1H), 4.84 (d, J=12 Hz, 1H), 4.33 (brs, 1H), 3.73-3.30 (m, 6H of piperidine), 2.89 (s, 3H), 2.43 (s, 3H), 1.71 (m, 1H); ESI-MS: m/z 476.08 [M+H]$^+$.

Synthesis of ether analog 7-((furan-2-yl)methoxy)-5-hydroxy-8-(3-hydroxy-1-methylpiperidin-4-yl)-2-methyl-4H-chromen-4-one (5)

This compound was synthesized using the similar procedure as described in example 2. White crystalline powder; $^1$H NMR (400 MHz, CD$_3$OD): δ 7.72 (d, J=1.2 Hz, 1H), 6.92 (d, J=3.2 Hz, 1H), 6.58 (dd, J=3.2, 1.6 Hz, 1H), 6.07 (s, 1H), 5.94 (s, 1H), 5.26 (d, J=14.4 Hz, 1H), 4.10 (d, J=14.4 Hz, 1H), 4.29 (brs, 1H), 3.71-3.50 (m, 6H of piperidin), 3.10 (s, 3H), 2.36 (s, 3H), 1.84 (m, 1H); $^{13}$C NMR (100 MHz, CD$_3$OD): δ 183.63, 172.27, 167.88, 162.01, 158.01, 157.96, 147.31, 144.93, 118.22, 112.58, 111.95, 108.22, 107.70, 103.10, 66.99, 65.17, 62.78, 58.35, 54.28, 37.44, 23.72, 21.55; ESI-MS: m/z 386.16 [M+H]$^+$.

Synthesis of ether analog 7-((thiophen-2-yl)methoxy)-5-hydroxy-8-(3-hydroxy-1-methylpiperidin-4-yl)-2-methyl-4H-chromen-4-one (6)

This compound was synthesized using the similar procedure as described in example 2. White powder; $^1$H NMR (400 MHz, CD$_3$OD): δ 7.69 (d, J=5.2 Hz, 1H), 7.54 (d, J=3.2 Hz, 1H), 7.19 (m, J=5.1, 3.1 Hz, 1H), 6.02 (s, 1H), 5.94 (s, 1H), 5.52 (d, J=13.6 Hz, 1H), 4.84 (brs, 1H), 3.81-3.31 (m, 6H of piperidine), 3.05 (s, 3H), 2.36 (s, 3H) 1.72 (m, 1H); ESI-MS m/z 403.17 [M+H]$^+$.

Synthesis of ether analog 7-(Cinnamyloxy)-5-hydroxy-8-(3-hydroxy-1-methylpiperidin-4-yl)-2-methyl-4H-chromen-4-one (7)

This compound was synthesized using the similar procedure as described in example 2. Yellow powder; m.p. 242-246° C.; $^1$H NMR (400 MHz, CD$_3$OD, ppm): δ 7.57 (m, 2H), 7.37 (m, 3H), 7.08 (d, J=15.6 Hz, 1H), 6.51 (m, J=15.6 Hz, 1H), 6.07 (s, 1H) 5.97 (s, 1H), 4.85 (m, 1H), 4.51 (m, 1H), 4.28 (brs, 1H), 3.78-3.33 (m, 6H of piperidine ring), 3.10 (s, 3H), 2.36 (s, 3H), 1.74 (m, 1H); $^{13}$C NMR (100 MHz, CD$_3$OD, ppm): δ 180.75, 165.22, 164.62, 159.96, 155.80, 140.84, 135.21, 128.6 (2C), 127.03 (2C), 117.2, 106.71, 106.60, 101.68, 101.22, 68.25, 64.8, 63.7, 62.4, 52.2, 36.1, 19.95, 19.76; ESI-MS: m/z 423.08 [M+H]$^+$.

Synthesis of ether analog 7-(4-Nitrobenzyloxy)-5-hydroxy-8-(3-hydroxy-1-methylpiperidin-4-yl)-2-methyl-4H-chromen-4-one (8)

This compound was synthesized using the similar procedure as described in example 2. White powder; m.p. 234-236° C.; $^1$H NMR (400 MHz, CD$_3$OD, ppm): δ 8.33 (d, J=8.4 Hz, 2H), 8.08 (d, J=8.4 Hz, 2H), 6.17 (m, 2H), 5.97 (d, J=12.8 Hz, 1H), 4.80 (d, J=12.8 Hz, 1H), 4.13 (brs, 1H), 3.77-3.35 (m, 6H of piperidine), 2.95 (s, 3H), 2.35 (s, 3H), 1.74 (m, 1H); $^{13}$C NMR (100 MHz, CD$_3$OD, ppm): δ 183.46, 176.22, 167.33, 162.22, 157.66, 149.16, 136.55 (2C), 124.89 (2C), 107.94, 107.88, 104.36, 104.03, 101.85, 70.89, 65.17, 64.55, 62.78, 57.29, 37.71, 21.73, 20.28; ESI-MS: m/z 441.1692 [M+H]$^+$.

Synthesis of ether analog 7-(2-Bromobenzyloxy)-5-hydroxy-8-(3-hydroxy-1-methylpiperidin-4-yl)-2-methyl-4H-chromen-one (9)

This compound was synthesized using the similar procedure as described in example 2. White powder; m.p. 238-241° C.; $^1$H NMR (400 MHz, CD$_3$OD, ppm): δ 8.10 (d, J=8.0 Hz, 1H), 7.83 (m, 1H), 7.48 (m, 2H), 5.98 (brs, 2H), 5.48 (d, J=13.2 Hz, 1H), 5.17 (d, J=13.3 Hz, 1H), 4.37 (brs, 1H), 3.95-3.59 (m, 6H of piperidine), 2.41 (s, 3H), 2.01 (s, 3H), 1.84 (m, 1H); $^{13}$C NMR (100 MHz, CD$_3$OD, ppm): δ 184.43, 169.35, 164.14, 161.97, 158.39, 137.24, 136.47, 135.66, 133.73, 129.69, 128.96, 108.81, 106.27, 105.51, 100.37, 72.14, 68.83, 66.74, 64.61, 53.39, 38.00, 21.31, 20.76; ESI-MS: m/z 474 [M+1]$^+$.

Synthesis of ether analog 7-((1H-Benzo[d]imidazol-2-yl)methoxy)-5-hydroxy-8-(3-hydroxy-1-methylpiperidin-4-yl)-2-methyl-4H-chromen-4-one (10)

This compound was synthesized using the similar procedure as described in example 2. White powder; m.p. 217-220° C.; $^1$H NMR (400 MHz, CD$_3$OD, ppm): δ 7.61 (dd, J=3.2, 6 Hz, 2H), 7.52 (dd, J=2.8, 6 Hz, 2H), 5.90 (s, 1H), 5.82 (s, 1H), 5.50 (d, J=13.6 Hz, 1H), 4.99 (d, J=13.6 Hz, 1H), 4.27 (brs, 1H), 3.91-3.26 (m, 6H of piperidin), 2.58 (s, 3H), 2.23 (s, 3H), 1.54 (m, 1H); ESI-MS: m/z 436.18 [M+H]$^+$.

Synthesis of ester analog 5-hydroxy-8-(3-hydroxy-1-methylpiperidin-4-yl)-2-methyl-4-oxo-4H-chromen-7-yl-furan-2-carboxylate (11)

This compound was synthesized using the similar procedure as described in example 2. White powder; m.p. 184-186° C.; $^1$H NMR (400 MHz, CD3OD, ppm): δ 7.73 (dd, J=0.4, 1.6 Hz, 1H), 7.49 (dd, J=0.8, 3.6 Hz, 1H), 6.60 (dd, J=1.6, 3.6 Hz, 1H), 6.22 (s, 1H), 5.96 (s, 1H), 5.58 (brs, 1H), 3.89-3.33 (m, 6H of piperidine), 2.97 (s, 3H), 2.14 (s, 3H), 2.10 (m, 1H); $^{13}$C NMR (100 MHz, CD$_3$OD, ppm): δ 184.16, 169.03, 164.07, 162.34, 158.66, 158.21, 148.77, 145.03, 120.90, 113.27, 108.67, 105.18, 104.62, 99.79, 70.35, 58.27, 56.92, 44.67, 36.52, 24.37, 20.47; IR (KBr): $\nu_{max}$ 3416, 2924, 1617, 1560, 1424, 1290, 1177, 1113 cm$^{-1}$; ESI-MS: m/z 400.16 [M+H]$^+$.

Synthesis of ester analog 5-hydroxy-8-(3-hydroxy-1-methylpiperidin-4-yl)-2-methyl-4-oxo-4H-chromen-7-yl-2-methylbenzoate (12)

This compound was synthesized using the similar procedure as described in example 2. White powder; m.p. 244-246° C.; $^1$H-NMR (400 MHz, CD$_3$OD, ppm): δ 8.03 (d, J=7.2 Hz, 1H), 7.36 (dd, J=7.2, 7.6 Hz, 1H), 7.23-7.13 (m, 2H), 6.187 (s, 1H), 5.83 (s, 1H), 5.61 (brs, 1H), 3.84-3.40 (m, 6H of piperidin), 2.94 (s, 3H), 2.17 (s, 3H), 2.08 (s, 3H), 2.03 (m, 1H); ESI-MS: m/z 424.46 [M+H]$^+$.

Example 3

General Procedure for the Synthesis of Baylis-Hilman Analogs 13-27

Figure 2:
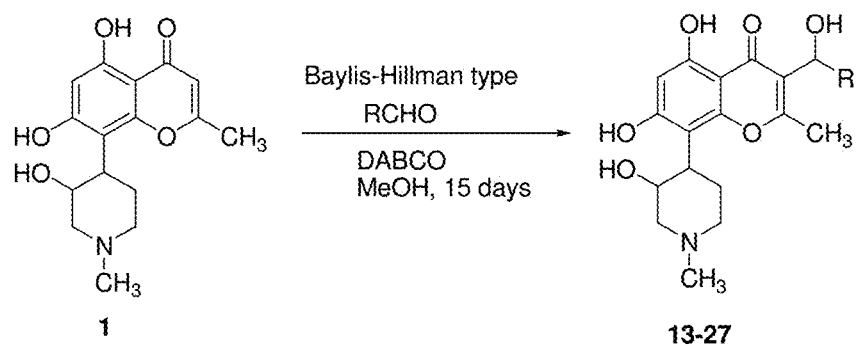
FIG. 2 is a diagram illustrating chemical synthesis of 5,7-dihydroxy-8-(3-hydroxy-1-methylpiperidin-4-yl)-2-methyl-4H-chromen-4-one compounds 13-27

A general synthetic strategy for Baylis-Hilman analogs 13-27 proposed in present invention is depicted in FIG. 2. Conditions used in the synthesis are mild and yields are excellent. The method of synthesis for compounds of the invention is as follows: To the solution of rohitukine (1, 61 mg, 2 mmol) in methanol (5 mL) was added substituted aromatic and aliphatic aldehydes (2 mmol) and DABCO (1 mmol), and the reaction mixture was continuously stirred for 10-15 days, however in none of the reaction starting material completely consumed, thus desired products were separated using preparative TLC.

Synthesis of Baylis-Hillman analog 5,7-dihydroxy-3-(hydroxy(4-nitrophenyl)methyl)-8-(3-hydroxy-1-methylpiperidin-4-yl)-2-methyl-4H-chromen-4-one (13)

This compound was synthesized using the procedure as described in example 3. Isolated as a racemic mixture; cream colored solid, $^1$H-NMR (400 MHz, DMSO-d$_6$): δ 13.57 (s, 1H), 8.13 (dd, J=4.8, 10 Hz, 2H), 7.71 (dd, J=4.4, 10.1 Hz, 2H), 5.91 (m, 2H), 3.94 (brs, 1H), 3.25-3.05 (m, 6H of piperidine), 2.60 (s, 3H), 1.88 (s, 3H), 1.27 (m, 1H); ESI-MS: m/z 457.16 [M+H]$^+$; IR (CHCl$_3$)$\nu_{max}$: 3400, 2923, 1658, 1556, 1468, 1389, 1273, 1150, 1025 (cm$^{-1}$).

Synthesis of Baylis-Hillman analog 3-((4-chlorophenyl)(hydroxy)methyl)-5,7-dihydroxy-8-(3-hydroxy-1-methylpiperidin-4-yl)-2-methyl-4H-chromen-4-one (14)

This compound was synthesized using the procedure as described in example 3. Isolated as a racemic mixture; white solid; $^1$H-NMR (400 MHz, CD$_3$OD): δ 7.34 (m, 2H), 7.12 (m, 2H), 5.92 (s, 1H), 5.84 (s, 1H), 4.07 (brs, 1H), 3.49 (d, J=12 Hz, 1H), 3.21 (d, J=12 Hz, 1H), 3.17-3.00 (m, 4H), 2.72 (s, 3H), 2.24 (s, 3H), 1.47 (d, J=12 Hz, 1H); ESI-MS: m/z 446.01 [M+H]$^+$; IR (CHCl$_3$) $\nu_{max}$: 3400, 2926, 1659, 1556, 1468, 1361, 1127, 1014 cm$^{-1}$.

Synthesis of Baylis-Hillman analog 3-((2-Bromophenyl)(hydroxy)methyl)-5,7-dihydroxy-8-(3-hydroxy-1-methylpiperidin-4-yl)-2 methyl-4H-chromen-4-one (15)

This compound was synthesized using the procedure as described in example 3. Isolated as a racemic mixture; off white solid; $^1$H NMR (400 MHz, CD$_3$OD): δ 7.51-7.06 (m, 4H), 6.37 (m, 1H), 5.88 (m, 1H), 4.17 (brs, 1H), 3.09-3.08 (m, 6H of piperidine), 2.96 (s, 3H), 2.32 (s, 3H), 1.60 (m, 1H); ESI-MS: m/z 491.8 [M+H]$^+$; IR (CHCl$_3$): $\nu_{max}$ 3391, 2923, 1658, 1558, 1465, 1387, 1273, 1149, 1026 cm$^{-1}$.

Synthesis of Baylis-Hillman analog 3-((3,5-difluorophenyl)(hydroxy)methyl)-5,7-dihydroxy-8-(3-hydroxy-1-methylpiperidin-4-yl)-2-methyl-4H-chromen-4-one (16)

This compound was synthesized using the procedure as described in example 3. Isolated as a racemic mixture; white solid; $^1$H NMR (CD$_3$OD, 400 MHz): δ 6.94 (M, 2H), 6.58 (m, 1H), 5.91 (s, 1H), 5.83 (s, 1H), 4.71 (brs, 1H), 4.03 (m, 1H), 3.48-2.91 (m, 5H), 2.74 (s, 3H), 2.23 (s, 3H), 1.48 (m, 1H); ESI-MS: m/z 448.2 [M+H]$^+$; IR (CHCl$_3$) $\nu_{max}$: 3391, 2924, 1659, 1557, 1463, 1388, 1272, 1113 cm$^{-1}$.

Synthesis of Baylis-Hillman analog 3-((3-Chlorophenyl)(hydroxy)methyl)-5,7-dihydroxy-8-(3-hydroxy-1-methylpiperidin-4-yl)-2-methyl-4H-chromen-4-one (17)

This compound was synthesized using the procedure as described in example 3. Isolated as a racemic mixture; white powder; ¹H NMR (400 MHz, DMSO-$d_6$): δ 13.46 (s, 1H), 7.47-7.17 (m, 4H), 5.91 (s, 1H), 5.97 (m, 1H) 3.88 (brs, 1H), 3.30-2.78 (m, 6H of piperidin), 2.51 (s, 3H), 2.24 (s, 3H), 1.13 (in, 1H).; ESI-MS: m/z 446.14 [M+H]⁺; IR (CHCl₃): $v_{max}$ 3400, 2925, 1659, 1470, 1388, 1273, 1150, 1027 cm⁻¹.

Synthesis of Baylis-Hillman analog 3-((3-bromo-4-methoxyphenyl)(hydroxy)methyl)-5,7-dihydroxy-8-(3-hydroxy-1-methyl-piperidin-4-yl)-2-methyl-4H-chromen-4-one (18)

This compound was synthesized using the procedure as described in example 3. Isolated as a racemic mixture; off white solid; ¹H NMR (500 MHz, CD₃OD): δ 7.75 (m, 1H), 7.37 (m, 1H), 6.89 (m, 1H), 5.97 (m, 1H), 5.88 (m, 1H), 4.08. (brs, 1H), 5.48 (d, 13.2 1H), 5.17 (d, J=13.3, 1H), 4.37 (brs, 1H), 3.73 (s, 3H) 3.35-2.80 (m, 6H of piperidin), 2.71 (s, 3H), 2.30 (s, 3H), 1.49 (m, 1H). ESI-MS: m/z 521.1 [M+H]⁺; IR (CHCl₃) $v_{max}$: 3400, 2928, 1659, 1552, 1494, 1394, 1272, 1149, 1080 cm⁻¹.

Synthesis of Baylis-Hillman analog 3-((3-Bromo-4-fluorophenyl)(hydroxy)methyl)-5,7-dihydroxy-8-(3-hydroxy-1-methylpiperidin-4-yl)-2-methyl-4H-chromen-4-one (19)

This compound was synthesized using the procedure as described in example 3. Isolated as a racemic mixture; white solid; ¹H NMR (400 MHz, DMSO-$d_6$): δ 7.70 (m, 1H), 7.42 (m, 1H), 7.23 (m, 1H), 5.92 (s, 1H), 5.75 (m, 1H), 4.00. (m, 1H), 3.34-2.51 (m, 6H of piperidin), 2.51 (s, 3H), 2.24 (s, 3H), 1.32 (m, 1H); ESI-MS: m/z 508.1 [M+H]⁺; IR (CHCl₃) $v_{max}$: 3400, 2926, 1658, 1455, 1389, 1243, 1145, 1083, 1023 cm⁻¹.

Synthesis of Baylis-Hillman analog 3-((2,6-dichlorophenyl)(hydroxy)methyl)-5,7-dihydroxy-8-(3-hydroxy-1-methylpiperidin-4-yl)-2-methyl-4H-chromen-4-one (20)

This compound was synthesized using the procedure as described in example 3. Isolated as a racemic mixture; white solid; ¹H NMR (500 MHz, CD₃OD): δ 7.89 (s, 1H), 7.30 (m, 1H), 7.17 (m, 1H), 6.91 (m, 1H), 5.93 (s, 1H), 4.20 (brs, 2H); 4.00-3.21 (m, 6H of piperidin), 3.18 (s, 3H), 2.35 (s, 3H), 1.82 (m, 1H). ESI-MS: m/z 478.1 [M+H]⁺; IR (CHCl₃) $v_{max}$: 3400, 2922, 1651, 1561, 1464, 1386, 1260, 1032 cm⁻¹.

Synthesis of Baylis-Hillman analog 3-((2-chloro-6-fluorophenyl)(hydroxy)methyl)-5,7-dihydroxy-8-(3-hydroxy-1-methylpiperidin-4-yl)-2-methyl-4H-chromen-4-one (21)

This compound was synthesized using the procedure as described in example 3. Isolated as a racemic mixture; white solid; ¹H NMR (500 MHz, DMSO-$d_6$): δ 13.15 (s, 1H), 7.28 (m, 2H), 7.61 (m, 1H), 6.32 (m, 1H), 5.87 (s, 1H), 4.04 (brs, 1H), 3.33-3.10 (m, 6H of piperidin), 2.75 (s, 3H), 2.27 (s, 3H), 1.44 (m, 1H); ESI-MS: m/z 464.1 [M+H]⁺.

Synthesis of Baylis-Hillman analog 5,7-dihydroxy-3-(hydroxy(5-nitrofuran-2-yl)methyl)-8-(3-hydroxy-1-methylpiperidin-4-yl)-2-methyl-4H-chromen-4-one (22)

This compound was synthesized using the procedure as described in example 3. Isolated as a racemic mixture; brown solid powder; ¹H NMR (400 MHz, CD₃OD): δ 7.21 (m, 1H), 6.30 (m, 1H), 6.26 (m, 2H), 4.68 (brs, 1H), 4.06-2.98 (m, 6H of piperidin), 2.73 (s, 3H), 2.22 (s, 3H), 1.50 (m, 1H). ESI-MS: m/z 447.2 [M+H]⁺; IR (CHCl₃): $v_{max}$ 3400, 2923, 1658, 1465, 1386, 1241, 1149, 1081, 1020 cm⁻¹.

Synthesis of Baylis-Hillman analog 3-((2,3-Dichlorophenyl)(hydroxy)methyl)-5,7-dihydroxy-8-(3-hydroxy-1-methylpiperidin-4-yl)-2-methyl-4H-chromen-4-one (23)

This compound was synthesized using the similar procedure as described in example 3. Isolated as a racemic mixture; solid powder; ¹H NMR (400 MHz, CD₃OD): δ 7.45 (m, 2H), 7.15 (m, 1H), 6.50 (m, 1H), 5.95 (brs 1H), 4.25 (brs, 1H), 3.68-3.32 (m, 6H of piperidin), 2.88 (s, 3H), 2.39 (s, 3H), 1.78 (m, 1H); ESI-MS: m/z 478.1 [M+H]⁺; IR (CHCl₃): $v_{max}$ 3400, 2923, 1658, 1556, 1466, 1387, 1242, 1101 cm⁻¹.

Synthesis of Baylis-Hillman analog 5,7-dihydroxy-8-(3-hydroxy-1-methylpiperidin-4-yl)-3-(1-hydroxydodecyl)-2-methyl-4H-chromen-4-one (24)

This compound was synthesized using the procedure as described in example 3. Isolated as a racemic mixture; white needles; ¹H NMR (400 MHz, CD₃OD): δ 6.56 (m, 1H), 5.83 (s, 1H), 4.75 (s, 1H), 4.05 (brs 1H), 3.49-2.80 (6H of piperidin), 2.63 (s, 3H), 2.24 (s, 3H), 2.14 (m, 2H), 1.39 (m, 1H), 1.20 (brs, 16H), 0.81 (m, 3H); ESI-MS: m/z 472.3 [M-OH]⁺; IR (CHCl₃) $v_{max}$: 2921, 1657, 1576, 1425, 1272, 1040 cm⁻¹.

Synthesis of Baylis-Hillman analog 3-((4-fluorophenyl)(hydroxy)methyl)-5,7-dihydroxy-8-(3-hydroxy-1-methylpiperidin-4-yl)-2-methyl-4H-chromen-4-one (25)

This compound was synthesized using the procedure as described in example 3. Isolated as a racemic mixture; white powder; ¹H NMR (500 MHz, CD₃OD): δ 7.40 (m, 2H), 6.97 (m, 2H), 5.89 (s, 1H), 5.69 (s, 1H), 3.93 (m, 1H), 3.23-2.57 (m, 6H of piperidin), 2.49 (s, 3H), 2.28 (s, 3H), 1.31 (m, 1H); ESI-MS: m/z 412.1 [M+H]⁺; IR (CHCl₃): $v_{max}$ 3400, 2927, 1658, 1602, 1549, 1425, 1342, 1040 cm⁻¹.

Synthesis of Baylis-Hillman analog 5,7-dihydroxy-3-(hydroxy(5-nitrothiophen-2-yl)methyl)-8-(3-hydroxy-1-methylpiperidin-4-yl)-2-methyl-4H-chromen-4-one (26)

This compound was synthesized using the procedure as described in example 3. Isolated as a racemic mixture; brown solid; ¹H NMR (CD₃OD, 400 MHz): δ 7.72 (d, J=2 Hz, 1H), 6.82 (d, J=2.1 Hz, 1H), 6.44 (s, 1H), 6.06 (s, 1H), 4.74 (brs, 1H), 4.19 (m, 1H), 3.66-3.20 (m, 5H), 2.82 (s, 3H), 2.34 (s, 3H), 1.71 (d, J=12 Hz, 1H); ESI-MS: m/z 463.13 [M+H]⁺; IR (CHCl₃) $v_{max}$: 3435, 2919, 2850, 1653, 1465, 1332, 1019 cm⁻¹.

Synthesis of Baylis-Hillman analog 5,7-Dihydroxy-3-(hydroxy(5-nitrothiophen-3-yl)methyl)-8-(3-hydroxy-1-methylpiperidin-4-yl)-2-methyl-4H-chromen-4-one (27)

This compound was synthesized using the procedure as described in example 3. Isolated as a racemic mixture;

brown colored solid; ¹H NMR (400 MHz, CD₃OD): δ 7.88 (m, 1H), 7.49 (m, 1H), 5.92 (m, 1H), 5.82 (m, 1H), 4.07 (brs, 1H), 3.49-2.98 (m, 6H of piperidin), 2.71 (s, 3H), 2.23 (s, 3H), 1.46 (m, 1H); ESI-MS: m/z 463.13 [M+H]⁺; IR (CHCl₃): ν$_{max}$ 3400, 2922, 1657, 1555, 1332, 1273, 1099, 1022 cm⁻¹.

General Procedure for the Synthesis of Styryl Analogs 28-35

Example 4

Figure 3:
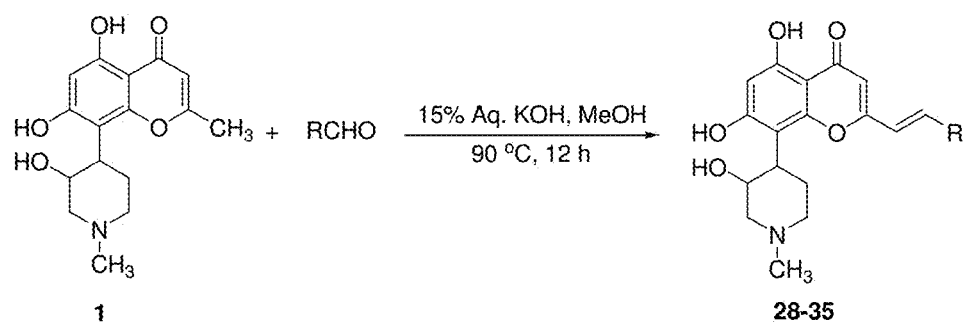
FIG. 3 is a diagram illustrating chemical synthesis of 5,7-dihydroxy-8-(3-hydroxy-1-methylpiperidin-4-yl)-2-methyl-4H-chromen-4-one compounds 28-35

A general synthetic strategy for styryl analogs 28-35 is depicted in FIG. 3. The method of synthesis for compounds of the invention is as follows: To the solution of rohitukine (1, 61 mg, 2 mmol) in methanol (5 mL) was added substituted aromatic or aliphatic aldehyde (2 mmol) in presence of 15% aqueous KOH (few drop) as catalyst, and the reaction mixture was continuously stirred for 10-20 h. The styryl products were observed as side products and their yields also varied depending on different aldehydes. An intense yellow colored band was separated using preparative TLC to get desired product.

Synthesis of styryl analog 2-(3-chlorostyryl)-5,7-dihydroxy-8-(3-hydroxy-1-methylpiperidin-4-yl)-4H-chromen-4-one (28)

This compound was synthesized using the procedure as described in example 4. Yellow solid; ¹H NMR (500 MHz, DMSO-d₆): δ 12.84 (s, 1H), 7.75 (s, 1H), 7.56-7.56 (m, 3H), 7.29 (d, J=16, 1H), 7.22 (d, J=16, 1H), 6.06 (s, 1H), 5.52 (s, 1H), 3.84 (brs, 1H), 3.19 (m, 1H), 2.97 (m, 1H), 2.89 (m, 1H), 2.77 (m, 1H), 2.26 (s, 3H), 2.20 (m, 2H), 1.19 (m, 1H); ESI-MS: m/z 428.1 [M+H]⁺; IR (CHCl₃): ν$_{max}$ 3391, 2923, 2357, 1733, 1699, 1652, 1575, 1386, 1046 cm⁻¹.

Synthesis of styryl analog 2-((E)-2-(anthracen-10-yl)vinyl)-5,7-dihydroxy-8-(3-hydroxy-1-methylpiperidin-4-yl)-4H-chromen-4-one (29)

This compound was synthesized using the procedure as described in example 4. Red solid; ¹H NMR (DMSO-d₆, 500 MHz): δ 8.68 (s, 1H), 8.34 (m, 3H), 8.16 (m, 2H), 7.61 (m, 4H), 7.00 (d, J=16 Hz, 1H), 6.21 (s, 1H), 5.56 (s, 1H), 3.9 (brs, 1H), 2.94-2.50 (m, 6H of piperidin), 2.05 (s, 3H), 1.28 (m, 1H); ESI-MS: m/z 494.19 [M+H]⁺; IR (CHCl₃): V$_{max}$ 3391, 2922, 2851, 2357, 1732, 1651, 1557, 1456, 1385, 1273, 1020 cm⁻¹.

Synthesis of styryl analog 2-(2-fluorostyryl)-5,7-dihydroxy-8-(3-hydroxy-1-methylpiperidin-4-yl)-4H-chromen-4-one (30)

This compound was synthesized using the procedure as described in example 4. Yellow solid; ¹H NMR (DMSO-d₆, 500 MHz): δ 7.86 (m, 1H), 7.52 (d, J=16 Hz, 1H), 7.05-7.54 (m, 3H), 7.17 (d, J=16 Hz, 1H), 6.05 (s, 1H), 5.32 (s, 1H), 4.53 (brs, 1H), 3.10-2.50 (m, 6H of piperidine), 2.05 (s, 3H), 1.14 (m, 1H); ESI-MS: m/z 412.1 [M+H]⁺; IR (CHCl₃): V$_{max}$ 3391, 2921, 2353, 1732, 1651, 1557, 1540, 1455, 1385, 1093 cm⁻¹.

Synthesis of styryl analog 2-styryl-5,7-dihydroxy-8-(3-hydroxy-1-methylpiperidin-4-yl)-4H-chromen-4-one (31)

This compound was synthesized using the procedure as described in example 4. Yellow solid; ¹H NMR (DMSO-d₆, 500 MHz): δ 7.61 (m, 2H), 7.44 (d, J=16 Hz, 1H), 7.30 (m, 3H), 6.92 (d, J=16 Hz, 1H), 6.09 (s, 1H), 5.91 (s, 1H), 4.17 (brs, 1H), 3.61. (m, 1H), 3.41 (m, 1H), 3.29 (m, 1H), 3.26 (m, 1H), 3.03 (m, 2H) 2.75 (s, 3H), 1.58 (m, 1H); ¹³C NMR (Pyridine-d₅, 125 MHz): δ 184.82, 169.46, 164.07, 163.34, 157.69, 138.96, 132.70, 131.42, 130.32, 122.96, 110.63, 110.61, 106.64, 103.87, 100.69, 71.29, 64.71, 59.08, 47.79, 40.79, 40.43, 27.10; ESI-MS: m/z 394.2 [M+H]⁺; IR (CHCl₃): ν$_{max}$ 3400, 2921, 1652, 1584, 1381, 1187, 1085 cm⁻¹.

Synthesis of styryl analog 2-(4-chlorostyryl)-5,7-dihydroxy-8-(3-hydroxy-1-methylpiperidin-4-yl)-4H-chromen-4-one (32)

This compound was synthesized using the procedure as described in example 4. Yellow solid; ¹H NMR (DMSO-d₆, 400 MHz): δ 7.24 (dd, J=4.0, 8.0 Hz, 2H), 7.22 (dd, J=4.0, 8.0 Hz, 2H), 7.16 (d, J=16 Hz, 1H), 6.31 (d, J=16 Hz, 1H), 6.12 (s, 1H), 5.91 (s, 1H), 4.02 (m, 1H), 4.13-3.12 (m, 6H of piperidine), 2.51 (s, 3H), 1.55 (m, 1H); ESI-MS: m/z 428.2 [M+H]⁺; IR (CHCl₃): ν$_{max}$ 3400, 2922, 2353, 1654, 1581, 1385, 1149, 1090 cm⁻¹.

Synthesis of styryl analog 2-(2,6-dichlorostyryl)-5,7-dihydroxy-8-(3-hydroxy-1-methylpiperidin-4-yl)-4H-chromen-4-one (33)

This compound was synthesized using the procedure as described in example 4. Yellow solid; ¹H NMR (DMSO-d₆, 400 MHz): δ 7.68 (m, 2H), 7.61 (d, J=16 Hz, 1H), 7.49 (t, J=8 Hz, 1H), 7.14 (d, J=16 Hz, 1H), 6.41 (s, 1H), 5.85 (s, 1H), 4.53 (brs, 1H), 3.10-2.50 (m, 6H of piperidine), 2.65 (s, 3H), 1.62 (m, 1H); ¹³C NMR (DMSO-d₆, 125 MHz): δ 179.68. 171.27, 159.20, 158.02, 154.03, 133.12, 131.49, 129.75, 128.35 (2C), 128.20, 127.90, 108.81, 106.79, 100.88, 100.52, 66.35, 59.82, 54.45, 43.15, 35.79, 22.01, 20.33, ESI-MS: m/z 462.01 [M+H]⁺; IR (CHCl₃): ν$_{max}$ 3400, 2921, 1652, 1577, 1550, 1417, 1380, 1191, 1085 cm⁻¹.

Synthesis of styryl analog 2-(2,3,4,5,6-pentafluorostyryl)-5,7-dihydroxy-8-(3-hydroxy-1-methylpiperidin-4-yl)-4H-chromen-4-one (34)

This compound was synthesized using the procedure as described in example 4. Yellow solid; ¹H NMR (DMSO-d₆, 400 MHz): δ 7.56 (d, J=16 Hz, 1H), 7.31 (d, J=16 Hz, 1H), 6.41 (s, 1H), 5.91 (s, 1H), 4.05 (m, 1H), 4.03-3.17 (m, 6H of piperidine), 2.51 (s, 3H), 1.55 (m, 1H); ESI-MS: m/z 484.2 [M+H]⁺; IR (CHCl₃): ν$_{max}$ 3400, 2922, 2356, 1652, 1475, 1366, 1279, 1116, 1035 cm⁻¹.

Synthesis of styryl analog 2-(3-fluorostyryl)-5,7-dihydroxy-8-(3-hydroxy-1-methylpiperidin-4-yl)-4H-chromen-4-one (35)

This compound was synthesized using the procedure as described in example 4. Yellow solid; ¹H NMR (DMSO-d₆, 400 MHz): δ 7-68-7.54 (m, 3H), 7.48 (d, J=16 Hz, 1H), 7.32 (m, 1H), 7.27 (d, J=16 Hz, 1H), 6.25 (s, 1H), 5.78 (s, 1H), 4.19 (s, 1H), 3.33 (m, 3H), 3.01-2.8 (m, 3H), 2.73 (s, 3H), 1.48 (m, 1H); ESI-MS: m/z 412.2 [M+H]⁺; IR (CHCl₃) Vmax: 3390, 2920, 2858, 2356, 1733, 1652, 1554, 1453, 1387, 1272, 1021 cm⁻¹.

Example 5

General Strategy for the Synthesis of Mannich Adducts 36-42

Figure 4:
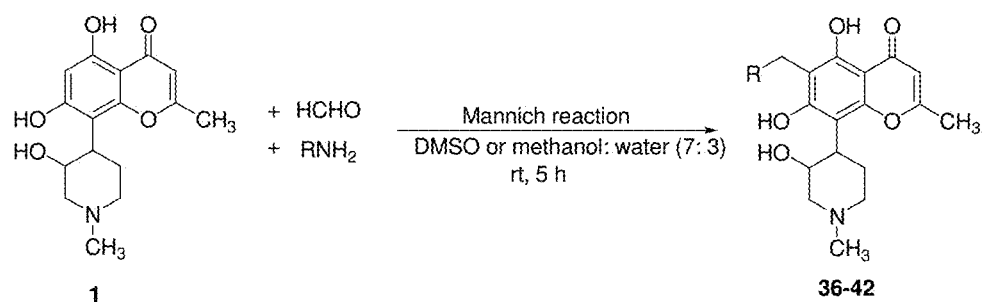
FIG. 4 is a diagram illustrating chemical synthesis of 5,7-dihydroxy-8-(3-hydroxy-1-methylpiperidin-4-yl)-2-methyl-4H-chromen-4-one compounds 36-42

A general synthetic strategy for Mannich adducts 36-42 is depicted in FIG. 4. The method of synthesis for compounds of the invention is as follows: To the solution of rohitukine (1, 61 mg, 2 mmol) in methanol-water (10 ml, ratio 7:3) was slowly added to a solution of formaldehyde (1 ml solution) and secondary amine (2 mmol) and reaction mixture was stirred at room temp for 5-10 h. Mannich adducts were purified using sephadex gel chromatography using methanol as a eluent.

Synthesis of Mannich adduct 5,7-dihydroxy-8-(3-hydroxy-1-methylpiperidin-4-yl)-2-methyl-6-(morpholinomethyl)-4H-chromen-4-one (36)

This compound was synthesized using the procedure as described in example 5 White solid; $^1$H NMR (400 MHz, CD$_3$OD): δ 5.90 (S, 1H), 4.1 (m, 3H), 3.77 (brs, 4H), 3.42 (d, J=12.1 Hz, 1H), 3.28 (d, J=12 Hz, 1H), 3.25 (d, J=12 Hz, 1H), 3.20-3.11 (m, 3H), 3.10 (brs, 4H), 2.56 (s, 3H), 2.25 (s, 3H), 1.55 (d, J=12 Hz, 1H); ESI-MS: m/z 403.20 [M−H]$^+$; IR (CHCl$_3$): ν$_{max}$ 3435, 2921, 2851, 1740, 1631, 1606, 1381, 1019 cm$^{-1}$.

Synthesis of Mannich adduct 5,7-dihydroxy-8-(3-hydroxy-1-methylpiperidin-4-yl)-2-methyl-6-((4-methylpiperazin-1-yl)methyl)-4H-chromen-4-one (37)

This compound was synthesized using the procedure as described in example 5. White solid; $^1$H-NMR (400 MHz, CD$_3$OD): δ 5.88 (s, 1H), 4.04 (m, 3H), 3.51 (d, J=12 Hz, 1H), 3.32 (d, J=12.1 Hz, 1H), 3.28 (d, J=12 Hz, 1H), 3.24-3.20 (m, 2H), 3.08 (brs, 4H), 2.81 (s, 3H), 2.56 (s, 6H), 2.25 (brs, 4H), 1.54 (d, J=12 Hz, 1H); ESI-MS: m/z 418.3 [M+H]$^+$; IR (CHCl$_3$) ν$_{max}$: 3400, 2923, 2852, 1738, 1659, 1606, 1391, 1362, 1319, 1149, 1042 cm$^{-1}$.

Synthesis of Mannich adduct 5,7-dihydroxy-8-(3-hydroxy-1-methylpiperidin-4-yl)-2-methyl-6-((piperidin-1-yl)methyl)-4H-chromen-4-one (38)

This compound was synthesized using the procedure as described in example 5. White solid; $^1$H-NMR (400 MHz, CD$_3$OD): δ 5.98 (s, 1H), 4.00 (m, 3H), 3.40-2.40 (m, 2H), 2.98 (m, 4H), 2.87 (m, 1H), 2.61-2.51 (m, 4H), 2.50 (s, 3H), 2.31 (s, 3H), 1.65 (m, 4H), 1.25 (brs, 1H), 0.85 (m, 2H); ESI-MS: m/z 403.3 [M+H]$^+$; IR (CHCl$_3$) ν$_{max}$: 3400, 2957, 2828, 2858, 1738, 1659, 1609, 1359, 1372, 1150 cm$^{-1}$.

Synthesis of Mannich adduct 5,7-dihydroxy-8-(3-hydroxy-1-methylpiperidin-4-yl)-2-methyl-6-((pyrrolidin-1-yl)methyl)-4H-chromen-4-one (39)

This compound was synthesized using the procedure as described in example 5. White solid; $^1$H NMR (400 MH$_z$, CD$_3$OD): δ 5.86 (s, 1H), 4.72 (brs, 3H), 4.16 (d, J=8 Hz, 1H), 3.51-3.05 (m, 7H), 2.76 (s, 3H), 2.26 (s, 3H), 1.99-1.85 (m, 6H), 151 (d, J=12 Hz, 1H); ESI-MS: m/z 389.2 [M+H]$^+$; IR (CHCl$_3$): ν$_{max}$ 3400, 2924, 2824, 1738, 1658, 1610.2, 1394, 1151, 1021 cm$^{-1}$.

Synthesis of Mannich adduct 6-((diethylamino)methyl)-5,7-dihydroxy-8-(3-hydroxy-1-methylpiperidin-4-yl)-2-methyl-4H-chromen-4-one (40)

This compound was synthesized using the procedure as described in example 5. White solid; $^1$H NMR (400 MH$_z$, CD$_3$OD): δ 5.88 (s, 1H), 4.15 (m, 3H), 3.32-3.05 (m, 10H), 2.79 (s, 3H), 2.29 (s, 3H), 1.51 (m, 1H), 1.26 (m, 6H); ESI-MS: m/z 391.10 [M+H]$^+$; IR (CHCl$_3$) ν$_{max}$: 3400, 2958, 29.27.5, 2958.16, 1738, 1660, 1610, 1274, 1153, 1019 cm$^{-1}$.

Synthesis of Mannich adduct 2-(N-((5,7-dihydroxy-8-(3-hydroxy-1-methylpiperidin-4-yl)-2-methyl-4-oxo-4H-chromen-6-yl)methyl)-N methylamino)acetic acid (41)

This compound was synthesized using the procedure as described in example 5. White needles; $^1$H NMR (400 MHz, CD$_3$OD): δ 6.01 (s, 1H), 4.28 (m, 2H), 3.68 (d, J=12.2 Hz, 1H), 3.57 (brs, 1H), 3.48 (d, J=12.3 Hz, 1H), 3.38 (m, 2H), 3.25-3.20 (m, 4H), 2.83 (s, 3H), 2.80 (s, 3H), 2.32 (s, 3H), 1.61 (d, J=13.3 Hz, 1H); ESI-MS: m/z 407.0 [M+H]$^+$; IR (CHCl$_3$) ν$_{max}$: 3400, 2922, 2852, 1741, 1618, 1609, 1384, 1021 cm$^{-1}$.

Synthesis of Mannich adduct 4-hydroxy-1-((5,7-dihydroxy-8-(3-hydroxy-1-methylpiperidin-4-yl)-2-methyl-4-oxo-4H-chromen-6-yl)methyl)pyrrolidine-2-carboxylic acid (42)

This compound was synthesized using the procedure as described in example 5. White crystalline solid; $^1$H NMR (400 MHz, CD$_3$OD): δ 6.01 (s, 1H), 4.31 (brs, 2H), 4.26 (s, 1H), 3.95 (d, J=8 Hz, 1H), 3.67 (d, J=12 Hz, 1H), 3.50-3.25 (m, 6H), 2.81 (s, 3H), 2.80 (m, 1H), 2.52 (m, 1H), 2.27 (s, 3H), 2.13 (d, J=12 Hz, 1H), 1.60 (d, J=12 Hz, 1H), 1.25 (m, 1H); ESI-MS: m/z 449.19 [M+H]$^+$; IR (CHCl$_3$): ν$_{max}$ 3435, 2922, 2852, 1739, 1589, 1418, 1219, 1019 cm$^{-1}$.

Example 6

Preparation of 2-(2,6-dichlorostyryl)-5,7-dihydroxy-8-(3-hydroxy-1-methylpiperidin-4-yl)-4H-chromen-4-one hydrochloride (33.HCl)

Compound 33 was dissolved in dry methanol and it was bubbled with HCl gas for 1 h. Hydrochloride salt of the compound was precipitated as yellow brown solid. $^1$H NMR (DMSO-d$_6$, 400 MHz): δ 7.63 (d, J=16 Hz, 1H), 7.54 (m, 2H), 7.38 (m, 1H), 7.00 (d, J=16 Hz, 1H), 6.51 (s, 1H), 6.30 (s, 1H), 4.09 (brs, 1H), 3.7-2.8 (m, 6H of piperidine), 2.69 (s, 3H), 1.11 (m, 1H).

Example 7

Preparation of 2-(2,3,4,5,6-pentafluorostyryl)-5,7-dihydroxy-8-(3-hydroxy-1-methylpiperidin-4-yl)-4H-chromen-4-one hydrochloride (34.HCl)

Compound 34 was dissolved in dry methanol and it was bubbled with HCl gas for 1 h. The hydrochloride salt of compound was precipitated as yellow brown solid. $^1$H NMR (DMSO-d$_6$, 400 MHz): δ 7.6 (d, J=16 Hz, 1H), 7.21 (d, J=16 Hz, 1H), 6.37 (s, 1H), 5.94 (s, 1H), 4.05 (m, 1H), 4.03-3.17 (m, 6H of pieridine), 2.31 (s, 3H), 1.21 (m, 1H).

TABLE 1

The summary of starting materials and reaction conditions used for preparation of compounds claimed in formula I (Scheme shown in FIG. 3). For preparation of compounds 28-35, general protocol is shown in example 4.

| Compound | Starting materials | Solvent | Reagents | Temperature |
|---|---|---|---|---|
| 28 | Rohitukine, 3-chlorobenzaldehyde | methanol or ethanol | 15% aq. KOH | 90° C. |
| 29 | Rohitukine, antracene benzaldehyde | methanol or ethanol | 15% aq. KOH | 80° C. |
| 30 | Rohitukine, 2-fluorobenzaldehyde | methanol or ethanol | 15% aq. KOH | 110° C. |
| 31 | Rohitukine, benzaldehyde | methanol or ethanol | 15% aq. KOH | 95° C. |
| 32 | Rohitukine, 4-chlorobenzaldehyde | methanol or ethanol | 15% aq. KOH | 120° C. |
| 33 | Rohitukine, 2,6 dichlorobenzaldehyde | methanol or ethanol | 15% aq. KOH | 100° C. |
| 34 | Rohitukine, 2,3,4,5,6 pentafluorobenzaldehyde | methanol or ethanol | 15% aq. KOH | 85° C. |
| 35 | Rohitukine, 3-fluorobenzaldehyde | methanol or ethanol | 15% aq. KOH | 105° C. |
| 33•HCl | Compound 33 | Dry methanol | HCl gas | 25° C. |
| 34•HCl | Compound 34 | Dry methanol | HCl gas | 30° C. |

All examples disclosed in formula II, are prepared by employing the similar method containing different $R_1$, $R_2$, $R_3$ and $R_4$ groups. For preparation of compounds 2-12, general protocol is shown in example 2. For preparation of compounds 13-27, general protocol is shown in example 3. For preparation of compounds 36-42, general protocol is shown in example 5. The details of reaction conditions are depicted in the Table 2 given below.

TABLE 2

The summary of starting materials and reaction conditions used for preparation of compounds claimed in formula II (Scheme shown in FIG. 1, 2, 4)

| Compound | Starting materials | Solvent | Reagents | Temperature/time |
|---|---|---|---|---|
| 2 | Rohitukine, Benzyl chloride | Without solvent | Potassium carbonate | 20° C., 10 min |
| 3 | Rohitukine, 4-methoxy benzyl bromide | Without solvent | Potassium carbonate | 25° C., 15 min |
| 4 | Rohitukine, 4-bromo benzyl bromide | Without solvent | Potassium carbonate | 27° C., 8 min |
| 5 | Rohitukine, 2-(bromo methyl)furan | Without solvent | Potassium carbonate | 20° C., 5 min |
| 6 | Rohitukine, 2-(bromo methyl)thiophene | Without solvent | Potassium carbonate | 30° C., 15 min |
| 7 | Rohitukine, cinnamyl bromide | Without solvent | Potassium carbonate | 25° C., 15 min |
| 8 | Rohitukine, 4-nitro benzyl bromide | Without solvent | Potassium carbonate | 25° C., 15 min |
| 9 | Rohitukine, 2-bromo benzyl bromide | Without solvent | Potassium carbonate | 30° C., 15 min |
| 10 | Rohitukine, 2-(bromo methyl)-1H-benzo[d]imidazole | Without solvent | Potassium carbonate | 25° C., 15 min |
| 11 | Rohitukine, furan-2-carbonyl chloride | Without solvent | Potassium carbonate | 25° C., 12 min |
| 12 | Rohitukine, 2-methyl benzoate | Without solvent | Potassium carbonate | 30° C., 15 min |
| 13 | Rohitukine, 4-nitro benzaldehyde | Methanol or ethanol | DABCO | 22° C., 15 days |
| 14 | Rohitukine, 4-chloro benzaldehyde | Methanol or ethanol | DABCO | 27° C., 10 days |
| 15 | Rohitukine, 2-bromo benzaldehyde | Methanol or ethanol | DABCO | 30° C., 12 days |
| 16 | Rohitukine, 3,5-difluorobenzaldehyde | Methanol or ethanol | DABCO | 30° C., 15 days |
| 17 | Rohitukine, 3-chloro benzaldehyde | Methanol or ethanol | DABCO | 25° C., 11 days |
| 18 | Rohitukine, 3-bromo 4-methoxy benzaldehyde | Methanol or ethanol | DABCO | 25° C., 15 days |
| 19 | Rohitukine, 3-bromo 4-fluoro benzaldehyde | Methanol or ethanol | DABCO | 25° C., 10 days |
| 20 | Rohitukine, 2,6-dichloro benzaldehyde | Methanol or ethanol | DABCO | 25° C., 14 days |
| 21 | Rohitukine, 2-fluoro-6-chlorobenzaldehyde | Methanol or ethanol | DABCO | 27° C., 15 days |
| 22 | Rohitukine, 5-nitro furan-2-carbaldehyde | Methanol or ethanol | DABCO | 20° C., 15 days |
| 23 | Rohitukine, 2,3-dichloro benzaldehyde | Methanol or ethanol | DABCO | 25° C., 15 days |
| 24 | Rohitukine, decanal | Methanol or ethanol | DABCO | 30° C., 14 days |
| 25 | Rohitukine, 4-fluorobenzaldehyde | Methanol or ethanol | DABCO | 30° C., 14 days |
| 26 | Rohitukine, 5-nitrothiophene-2-carbaldehyde | Methanol or ethanol | DABCO | 25° C., 15 days |
| 27 | Rohitukine, 4-nitrothiophene-2-carbaldehyde | Methanol or ethanol | DABCO | 25° C., 15 days |
| 36 | Rohitukine, morpholine | Methanol-water (ratio 7:3) or DMSO | Formaldehyde | 27° C., 10 h |
| 37 | Rohitukine, N-methyl-piperazine | Methanol-water (ratio 7:3) or DMSO | Formaldehyde | 30° C., 5 h |
| 38 | Rohitukine, piperidine | Methanol-water (ratio 7:3) or DMSO | Formaldehyde | 30° C., 10 h |
| 39 | Rohitukine, pyrrolidine | Methanol-water (ratio 7:3) or DMSO | Formaldehyde | 25° C., 8 h |
| 40 | Rohitukine, diethylamine | Methanol-water (ratio 7:3) or DMSO | Formaldehyde | 25° C., 8 h |
| 41 | Rohitukine, sarcosin | Methanol-water (ratio 7:3) or DMSO | Formaldehyde | 27° C., 10 h |
| 42 | Rohitukine, 4-hydroxyproline | Methanol-water (ratio 7:3) or DMSO | Formaldehyde | 20° C., 10 h |

Example 8

Cytotoxicity of Compounds of the Invention

Compounds proposed in the present invention were evaluated for their cytotoxic effect against panel of six cancer cell line viz. HL-60 (Leukemia), PC-3 (Prostate), A-375 (Melanoma), MIAPaCa-2 (pancreatic), MCF-7 (Breast) and Caco-2 (Colon) using MTT assay. In each well of a 96-well plate, $3 \times 10^3$ cells were grown in 100 μL of medium. After 24 h, each test molecules were added to achieve a final concentration of 10 to 0.01 μmol/L, respectively. After 48 h of treatment, 20 μL of 2.5 mg/mL MTT (Organics Research, Inc.) solution in phosphate buffer saline was added to each well. After 48 h, supernatant was removed and formazan crystals were dissolved in 200 μL of DMSO. Absorbance was then measured at 570 nm using an absorbance plate reader (Bio-Rad Microplate Reader). Data are expressed as the percentage of viable cells in treated relative to non-treated conditions. Each experiment was repeated thrice and data was expressed as mean±SD of three independent experiments (*Mol. Cancer Ther.* 2010, 9, 358-368). Rohitukine (1) along with several analogs showed promising cytotoxicity in panel of cell lines. Cytotoxicity results are shown in Table 3 and 4.

The present invention is related to novel compounds that show promising anticancer and CDK inhibitory activities. Both series of compounds displayed cytotoxicity against a panel of cell lines including HL-60 (leukemia), PC-3 (prostate), A-375 (Melanoma), MIAPaCa-2 (pancreatic), MCF-7 (breast) and Caco-2 (colon) as shown in Table 3 and 4. The styryl analogs 31 and 33 displayed promising cytotoxicity in HL-60 cells with $IC_{50}$ value of 1.0 and 0.9 μM, respectively. Another styryl analog 28 displayed potent cytotoxicity in MCF-7 cells with $IC_{50}$ value of 2

TABLE 4

$IC_{50}$ (μM) values of selected compounds of invention on selected cell lines[a]

| Compound code | HL-60 Leukemia | PC-3 Prostate | A-375 Melanoma | MCF-7 Breast | Caco-2 Colon |
|---|---|---|---|---|---|
| 1 | 6 | ND | ND | ND | ND |
| 6 | ND | ND | 8 | ND | ND |
| 9 | ND | ND | 12 | ND | ND |
| 10 | 8 | ND | ND | ND | ND |
| 14 | 11 | ND | ND | ND | ND |
| 20 | ND | 5 | ND | ND | ND |
| 28 | ND | 10 | 4 | 2 | ND |
| 29 | ND | 12 | ND | ND | ND |
| 30 | 8 | 7 | 7 | 3 | 8 |
| 31 | 1 | 58 | 4.4 | 31 | 3.7 |
| 32 | 8 | 31 | 30 | 49 | 5.6 |
| 33 | 0.9 | 41 | 8 | 4 | 7 |
| 34 | 3 | 30 | 8 | 4 | 7 |

ND, not determined;
[a]Since none of the compound showed >50% growth inhibition in MIAPaCa-2 cell line in preliminary screening at 10 μM, no $IC_{50}$ was determined in this cell line.

Example 9

Inhibition of CDK-2/Cyclin a by Compounds of the Invention

Figure 5:
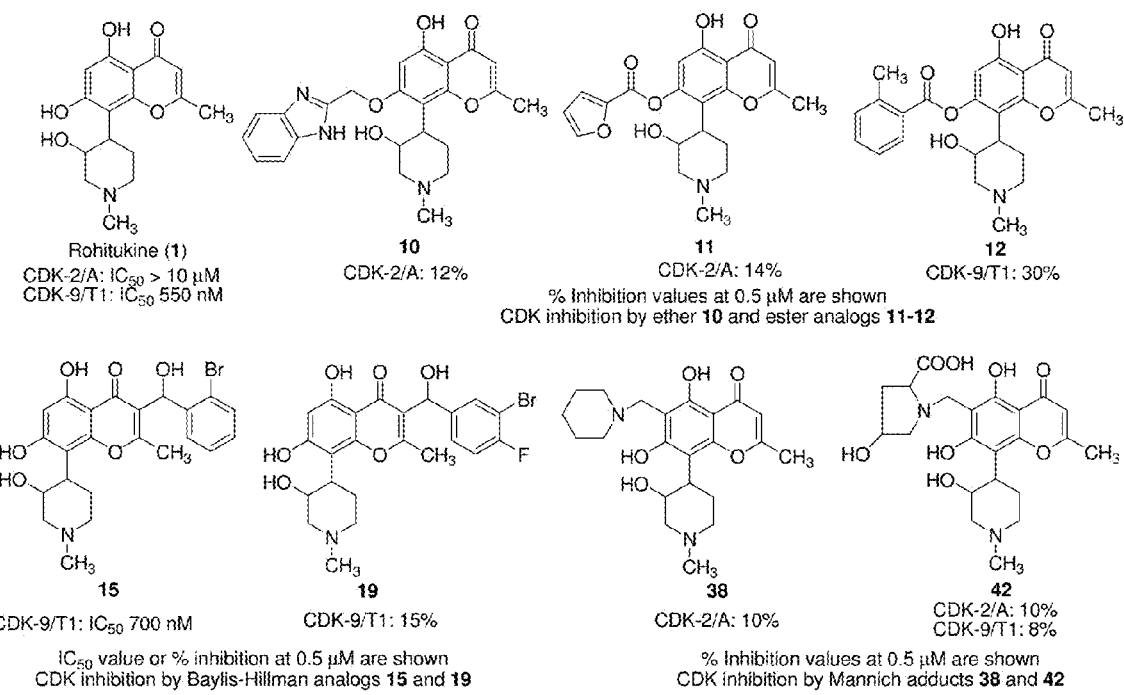
FIG. 5 is a diagram illustrating cyclin-dependent kinase (CDK) inhibition by 5,7-dihydroxy-8-(3-hydroxy-1-methyl-piperidin-4-yl)-2-methyl-4H-chromen-4-one compounds 1, 10-12, 15, 19, 38 and 42
Figure 6:
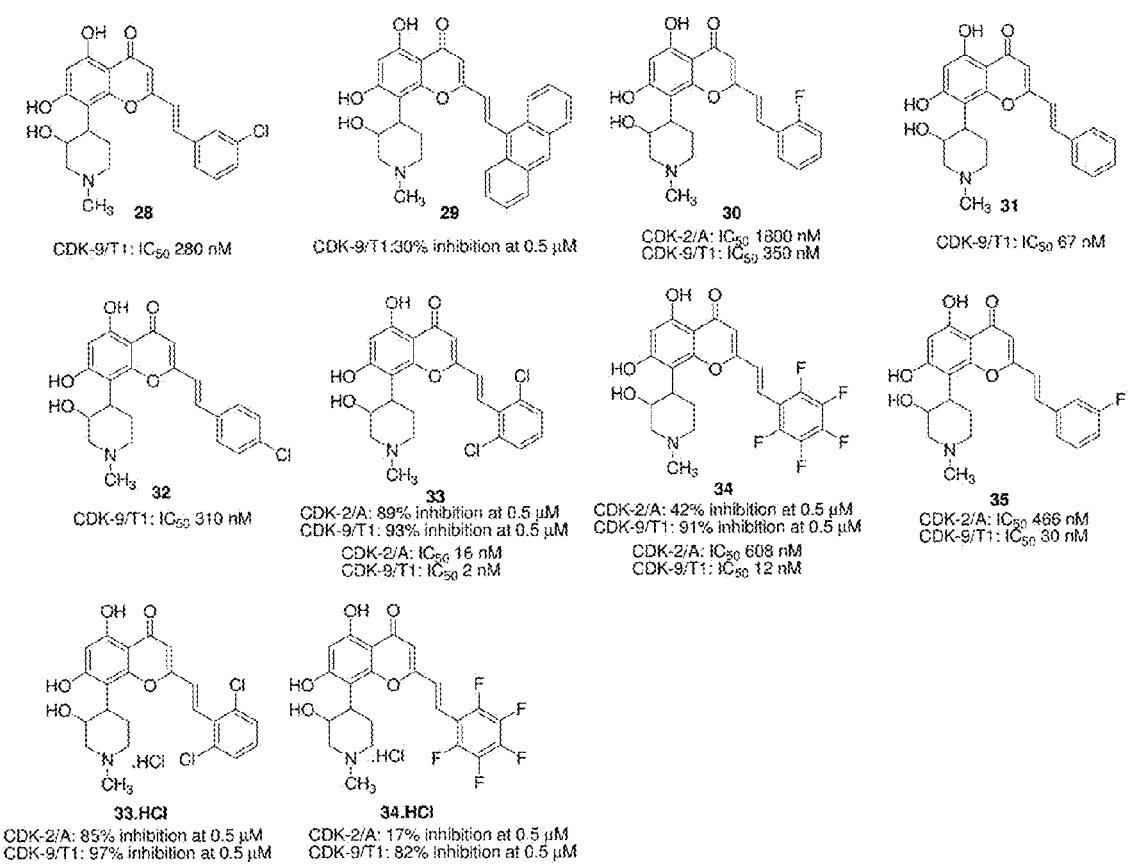
FIG. 6 is a diagram illustrating cyclin-dependent kinase (CDK) inhibition by 5,7-dihydroxy-8-(3-hydroxy-1-methyl-piperidin-4-yl)-2-methyl-4H-chromen-4-one compounds 28-35

CDK-2/cyclin A (5-20 mU diluted in 50 mM Hepes pH 7.5, 1 mM DTT, 0.02% Brij35, 100 mM NaCl) was assayed against Histone H1 in a final volume of 25.5 μl containing 50 mM Hepes pH7.5, 1 mM DTT, 0.02% Brij35, 100 mM NaCl, Histone H1 (1 mg/ml), 10 mM magnesium acetate and 0.02 mM [33P-g-ATP](500-1000 cpm/pmole) and incubated for 30 min at room temperature. Assays were stopped by addition of 5 μl of 0.5 M (3%) orthophosphoric acid and then harvested onto P81 Unifilter plates with a wash buffer of 50 mM orthophosphoric acid. CDK-2/A inhibitory activity of rohitukine and its analogs is shown in FIGS. 5 and 6.

TABLE 3

Cytotoxicity of selected compounds of invention against panel of cancer cell lines:

| | | Cell Growth Inhibition (%) | | | | | |
|---|---|---|---|---|---|---|---|
| Sample code | Conc (μM) | HL-60 Leukemia | PC-3 Prostate | A-375 Melanoma | MIAPaCa-2 Pancreatic | MCF-7 Breast | Caco-2 Colon |
| 1 | 10 | 83.32 | 32.87 | 41.24 | 1.46 | 15.36 | 11.86 |
| 2 | 10 | 24.30 | 41.00 | 27.79 | 13.80 | 1.44 | 17.65 |
| 3 | 10 | 22.79 | 35.23 | 34A6 | 15.71 | 15.61 | 8.43 |
| 4 | 10 | 26.95 | 17.08 | 45.49 | 13.15 | 14.03 | 13.03 |
| 5 | 10 | 31.88 | 14.06 | 36.82 | 6.61 | 5.73 | 16.86 |
| 6 | 10 | 22.24 | 22.76 | 53.80 | 13.25 | 19.82 | 33.29 |
| 7 | 10 | 20.98 | 18.26 | 21.78 | 11.19 | 7.02 | 9.49 |
| 8 | 10 | 14.40 | 22.98 | 37.52 | 12.36 | 39.30 | 13.59 |
| 9 | 10 | 3.05 | 31.74 | 58.62 | 29.69 | 45.38 | 35.10 |
| 11 | 10 | 80.21 | 15.08 | 11.21 | 16.05 | 2.86 | 1.96 |
| 12 | 10 | 12.83 | 18.58 | 42.03 | 7.19 | 13.44 | 6.53 |
| 13 | 10 | 0 | 23.84 | 35.85 | 2.48 | 4.03 | 5.08 |
| 14 | 10 | 1.93 | 41.02 | 34.19 | 14.81 | 5.91 | 2.83 |
| 15 | 10 | 52.02 | 44.52 | 22.44 | 10.10 | 20.58 | 6.62 |
| 17 | 10 | 22.24 | 30.98 | 34.91 | 1.52 | 5.01 | 4.42 |
| 21 | 10 | 25.37 | 72.48 | 20.80 | 8.58 | 13.61 | 5.94 |
| 28 | 10 | 24.31 | 53.66 | 65.87 | 40.32 | 80.39 | 27.52 |
| 29 | 10 | 12.05 | 50.54 | 4.963 | 16.98 | 12.69 | 0.00 |
| 30 | 10 | 80.45 | 72.16 | 54.10 | 21.26 | 81.13 | 51.00 |

Example 10

Inhibition of CDK-9/Cyclin T1 by Compounds of the Invention

CDK-9/Cyclin T1 (5-20 mU diluted in 50 mM Tris pH 7.5, 0.1 mM EGTA, 1 mg/ml BSA, 0.1% mercaptoethanol) was assayed against a substrate peptide (YSPTSPSYSPTSP-SYSPTSPKKK) in a final volume of 25.5 µl containing 50 mM Tris pH 7.5, 0.1 mM EDTA, 10 mM DTT, 1 mg/ml BSA, 0.3 mM YSPTSPSYSPTSPSYSPTSPKKK, 10 mM magnesium acetate and 0.05 mM [33P-γ-ATP] (50-1000 cpm/pmole) and incubated for 30 mM at room temperature. Assays were stopped by addition of 5 µl of 0.5 M (3%) orthophosphoric acid and then harvested onto P81 Unifilter plates with a wash buffer of 50 mM orthophosphoric acid. CDK-9/T1 inhibitory activity of rohitukine and its analogs is shown in FIGS. 5 and 6.

The CDK inhibition profile of compounds of the formulae I and II is shown in FIGS. 5 and 6. Amongst various analogs presented in this invention, styryl series of compounds 28-35 showed promising activity against CDK-2 and CDK-9 showing $IC_{50}$ values in low nanomolar range. Analogs 33, 34 and 35 are potent inhibitors of both enzymes CDK-2 and CDK-9 displaying $IC_{50}$ values in the range of 16-608 nM for CDK-2 and 2-30 nM for CDK-9, respectively. The comparative CDK-2 and CDK-9 inhibitory activity of rohitukine (1), flavopiridol and new most potent analogs 33-35 of the present invention is shown in Table 5. Results presented in table 3 indicate that synthesized NCEs have better CDK inhibitory activity compared with parent natural product rohitukine (1).

TABLE 5

Comparative CDK-2 and CDK-9 inhibitory activity of rohitukine (1), flavopiridol and new most potent analogs 33-35 of the present invention

| Compound | Structure | $IC_{50}$ (nM) CDK-2/A | $IC_{50}$ (nM) CDK-9/TI |
|---|---|---|---|
| Rohitukine (1) | [chromone structure with OH, HO, HO, piperidine-N-CH3, CH3] | >10,000 | 550 |
| Flavopiridol | [chromone structure with OH, HO, HO, piperidine-N-CH3, 2-chlorophenyl] | 170 (Kim K.S. et al., J. Med. Chem. 2000, 43, 4126) | 20 (Montagnoli A. et al., Nat. Chem. Biol. 2008, 4, 357) |
| 33 | [chromone structure with OH, HO, HO, piperidine-N-CH3, 2,6-dichlorostyryl] | 16 | 2 |

TABLE 5-continued

Comparative CDK-2 and CDK-9 inhibitory activity of rohitukine (1), flavopiridol and new most potent analogs 33-35 of the present invention

| Compound | Structure | IC$_{50}$ (nM) CDK-2/A | CDK-9/TI |
|---|---|---|---|
| 34 | (structure shown) | 608 | 12 |
| 35 | (structure shown) | 466 | 30 |

Figure 7:
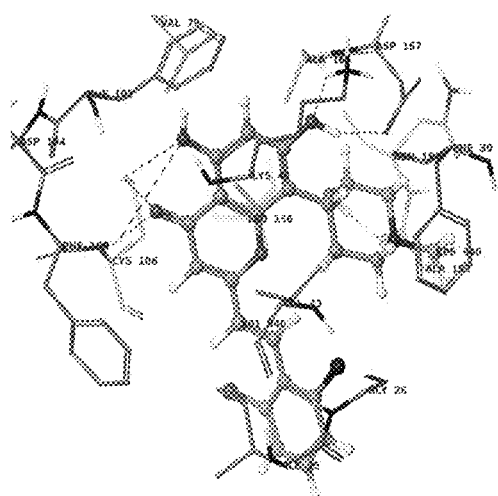
FIG. 7 is a diagram showing interactions of compounds 33 and 34 with the active site of CDK-9
Figure 7:
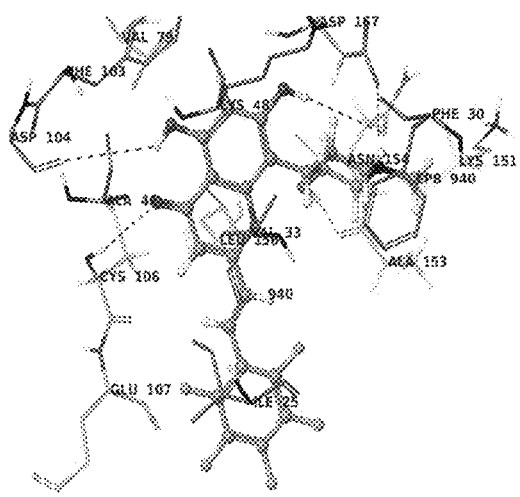

The interactions and binding pattern of compounds 33 and 34 with the active site of CDK-9 was studied (FIG. 7). It is well known that, binding of the CDK-9 inhibitor flavopiridol to CDK-9 induces conformational changes in the CDK-9/cyclin T complex, which bury flavopiridol deeply in the ATP binding site (Baumli S. et al. *EMBO J.* 2008, 23, 1907-1918) and prevent subsequent phosphorylation by blocking the entry of ATP in competitive manner. The flavopiridol-CDK-9 crystal structure (PDB ID: 3BLR) was used to study interactions of compounds 33 and 34 with CDK-9 active site. Similar to the flavopiridol, both compounds showed binding to the ATP binding site of CDK-9/Cyclin T complex by dense network of H-bonding and Vander waal interactions. Like flavopiridol, the carbonyl oxygen and C-5 hydroxyl oxygen of compound 33 interacts with the —SH and NH group of Cys106 residue of hinge region with plethora of H-bonding. Protonated piperidinyl NH$^+$ and piperidinyl 3'-hydroxyl group interacts with the Ala153 and C7 hydroxyl group with backbone and side chain Asp167 of DFG signature motif. Instead of chloro-phenyl ring of flavopiridol, compound 33 bears trans-2,6-dichloro-styryl ring, which interacts with the closed G loop residues including Gly26, Ile 25 and Val 33 by Vander waal interactions. All the interactions with the compound 33 are shown in FIG. 7. Compound 34 binds to same ATP binding site but slightly deeper into the hinge region pocket. In compound 34, the hydrogen atom of C-5 hydroxyl group interacts with the Asp104 back bone and carbonyl oxygen with Cys106 by H-bonding. However, instead of C-7 hydroxyl group interactions to Asp167, compound 34 interacts with the Asn154 residue and protonated piperidinyl NH$^+$ interacts with the Asp167 residue of DFG signature motif. The 2,3,4,5,6-pentafluoro styryl moiety at C-2 carbon displayed similar vander waal interactions with CDK-9/cyclinT complex as that of flavopiridol and compound 33 (FIG. 7).

The potent CDK inhibitory properties of the compounds of the invention can therefore be used to treat or prevent diseases, disorders, conditions, or symptoms in a patient (e.g. human) that involve, directly, or indirectly abnormal cellular proliferation.

Example 11

In Vivo Anticancer Activity of Compound 33 in Ehrlich Solid Tumor Mice Model

Ehrlich ascites carcinoma (EAC) cells were collected from the peritoneal cavity of the swiss mice harbouring 8-10 days old ascitic tumor. $1 \times 10^7$ EAC cells were injected intramuscularly in right thigh of 31 Swiss male mice selected for the experiment on day 0. The next day, animals were randomized and divided into four groups. Three treatment groups contained 7 animals each and one control group contained 10 animals. Treatment was given as follows:

Group I: Compound 33 (50 mg/kg i/p) from day 1-9.
Group II: Compound 33 (70 mg/kg i/p) from day 1-9.

The third treatment group was treated with 5-fluorouracil (22 mg/kg, i.p) from day 1-9 and it served as positive control. The control group was similarly administered normal saline (0.2 ml, i.p.) from day 1-9. On day 9 & 13, tumor bearing thigh of each animal was shaved and longest and shortest diameters of the tumor were measured with the help of vernier caliper. Tumor weight of each animal was calculated using the following formula.

$$\text{Tumor weight (mg)} = \frac{\text{Length (mm)} \times [\text{width (mm)}]^2}{2}$$

The percent tumor growth inhibition was calculated on day 13 by comparing the average values of treated groups with that of control group. Tumor growth in saline treated control animals was taken to be 100%.

Compound 33 was screened for in vivo anticancer activity in Ehrlich solid tumor mice model. Results are shown in Table 6. Compound 33 at 70 mg/kg administered intraperitonially showed 37.65% tumor growth inhibition without any mortality.

TABLE 6

In-vivo anticancer activity of compound 33 in Ehrlich solid tumor mice model

| Treatment Groups | Av. Body weights (g) of animals on days | | | Day 13 | | | |
|---|---|---|---|---|---|---|---|
| | 1 | 5 | 9 | Av. Body weights (g) | Av. Tumor weights (mg) | % Tumor Growth Inhibition | Mortality |
| Compound 33 (50 mg/kg i/p) | 21.21 | 21.92 | 22.30 | 22.46 | 989.12 ± 115.22 | 33.11 | 0/7 |
| Compound 33 (70 mg/kg i/p) | 20.57 | 21.4 | 22.0 | 21.85 | 922.0 ± 88.18 | 37.65 | 0/7 |
| Positive control 5-FU (22 mg/Kg i/p) | 20.54 | 21.28 | 20.0 | 19.85 | 613.71 ± 61.72 | 58.50 | 0/7 |
| Normal Control NS (0.2 ml i/p) | 21.8 | 23.1 | 23.1 | 23.4 | 1478.9 ± 125.99 | — | 0/10 |

TABLE 7

Solubility of compounds 33-34 and their hydrochloride salts in water, phosphate buffer saline (PBS), simulated gastric fluid (SGF), and simulated intestinal fluid (SIF).

| Compound | Solubility in µg/mL | | | |
|---|---|---|---|---|
| | Water | PBS | SGF | SIF |
| 33 | 5 | 5 | 40 | 20 |
| 34 | 5 | 10 | 80 | 20 |
| Hydrochloride salt of 33 | >1500 | 40 | 40 | 10 |
| Hydrochloride salt of 34 | >1500 | 40 | 80 | 40 |

Example 12

Determination of Thermodynamic Equilibrium Solubility

The compounds were first dissolved in methanol to prepare stock solutions (100 and 1000 µg/mL). Different concentrations of stock solutions were pipetted into the 96-well plates and the solvent was evaporated to ensure that solid drug was present in the beginning of the experiment. Thereafter, 200 µl of the dissolution medium (water) was added to the wells and 96-well plate was shaken horizontally at 300 rpm (Eppendorf Thermoblock Adapter, North America) for 4 h at room temperature (25±1° C.). The plates were kept overnight for equilibration of drug in medium. Later, the plates were centrifuged at 3000 rpm for 15 min (Jouan centrifuge BR4i). Supernatant (50 µl) was pipetted into UV 96-well plates (Corning® 96 Well Clear Flat Bottom UV-Transparent Microplate) for analyses with plate reader (SpectraMax Plus384) at $\lambda_{max}$ of 350 nm. The analyses were performed in triplicate for each compound. The solubility curve of concentration (µg/mL) vs absorbance was plotted to find out saturation point and the corresponding concentration was noted (Heikkilä, T. et al. *Int. J. Pharm.* 2011, 405, 132).

The aqueous solubility of best compounds 33 and 34 and their hydrochloride salts was determined using 96-well plate assay. Results are shown in Table 7. Both hydrochloride salts showed improved water solubility.

Example 13

Molecular Modeling of Compound 33 and 34 with Cyclin-Dependent Kinase 9

CDK-9/cylin T/flavopiridol complex was retrieved from the protein data bank (PDB ID: 3BLR), prepared by protein preparation wizard in maestro (Polier G. et al. *Cell Death Dis.* 2011, 2, 1-10). The site of molecular docking was defined by constructing the grid considering flavopiridol as centroid of grid box. All docking calculations were done using GLIDE XP docking, and ΔG of inhibitors binding to CDK-9/cyclin T complex was carried out by Prime using end point MMGB/SA method.

ADVANTAGES OF THE INVENTION

The main advantages of the present invention are:
The method for synthesis of compounds of the invention uses very mild conditions and produce higher yields.
Compounds of the invention are very potent inhibitors of cyclin-dependent kinases, which are implicated in the pathogenesis of cancer and HIV infection.
Compounds of the invention show promising in-vitro antiproliferative activity at micromolar to nanomolar concentrations.
Compounds of the invention show promising in-vivo anticancer activity in Ehrlich solid tumor mice model.
Compounds of the invention have good water solubility and are stable.

We claim:

1. A compound of formula A and a pharmaceutically acceptable salt thereof,

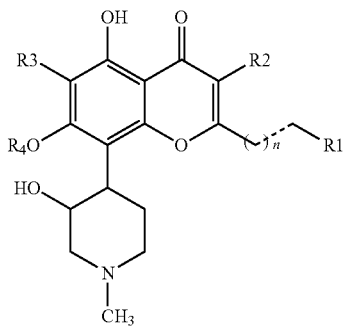

Formula A wherein,
- n=1, the dotted line indicates a double bond,
- $R_1$ is selected from the group consisting of substituted aryl, fused aryl, heteroaryl, substituted heteroaryl, wherein the substituents are selected from the group consisting of halogen, nitro, amino, substituted amino, hydroxyl, alkoxy, carboxyl, and COO-alkyl C1-C4 wherein alkyl is long chain or branched,
- $R_2$, $R_3$ and $R_4$ is hydrogen.

2. The compound of formula A and a pharmaceutically acceptable salt thereof as claimed in claim 1, wherein structural formula of the representative compounds are having the following formulae:

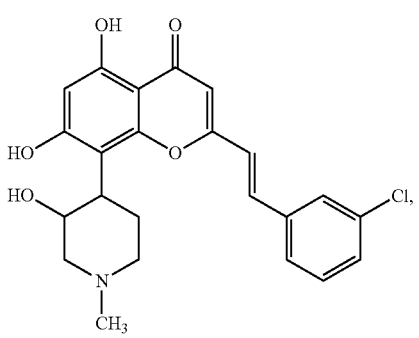

28

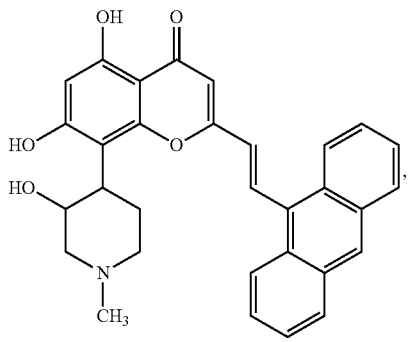

29

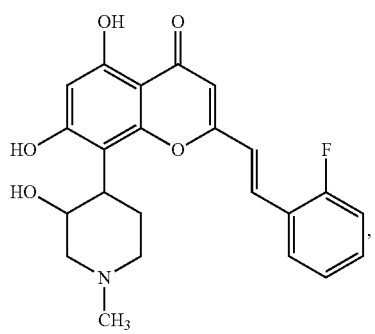

30

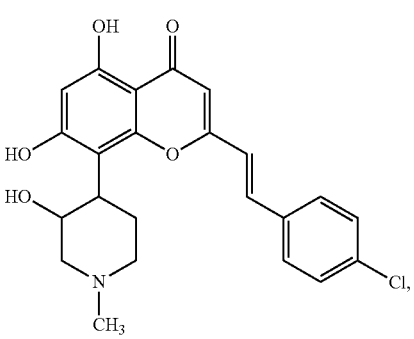

32

-continued

33
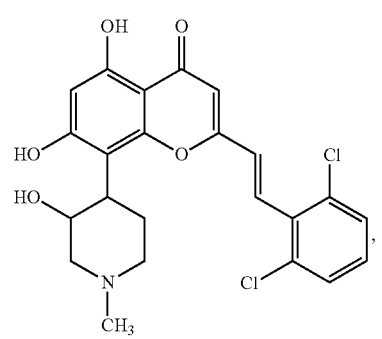

34
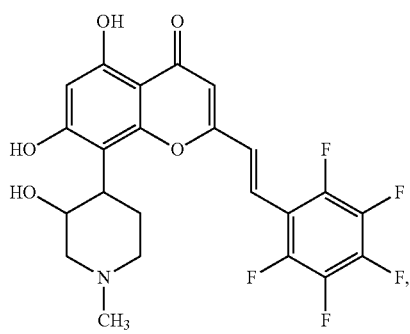

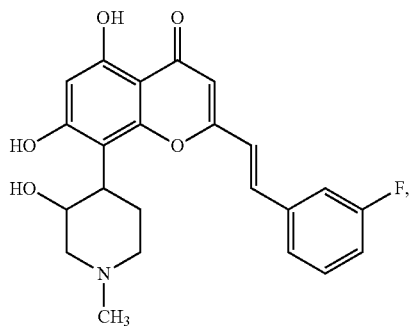

33·HCl
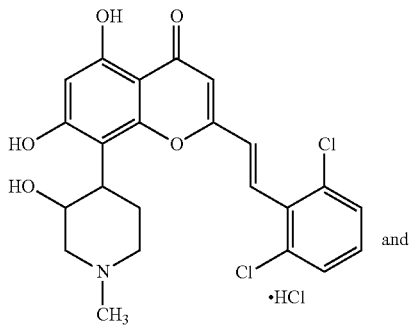
and

34·HCl
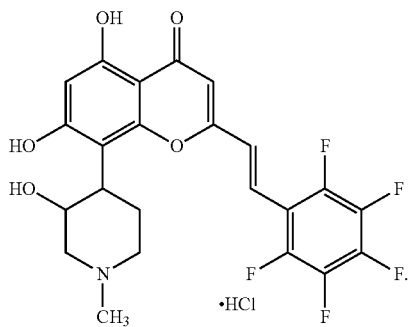

3. The compound of formula A and a pharmaceutically acceptable salt thereof as claimed in claim 1, wherein salts of said compounds are selected from the group consisting of hydrochloride, hydrobromide, and methane sulfonate.

4. A process for the preparation of compounds of formula A,

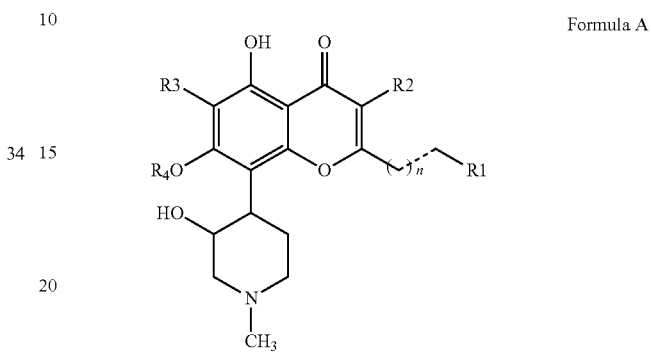

Formula A wherein, n=1, the dotted line indicates a double bond, $R_1$ is selected from the group consisting of substituted aryl, fused aryl, heteroaryl, substituted heteroaryl, wherein the substituents are selected from the group consisting of and halogen, nitro, amino, substituted amino, hydroxyl, alkoxy, carboxyl, and COO-alkyl C1-C4 wherein alkyl is long chain or branched, $R_2$, $R_3$ and $R_4$ is hydrogen;

wherein said process comprises the step of reacting Rohitukine

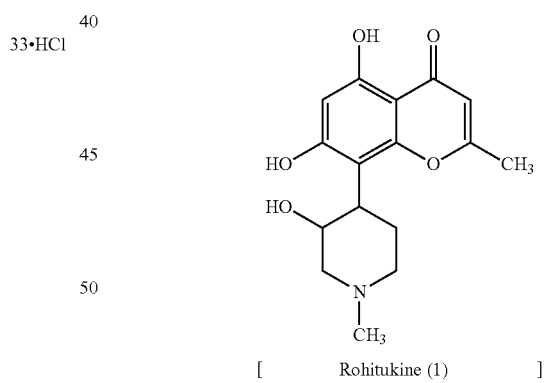

[ Rohitukine (1) ]

with a substituted aromatic aldehyde in the presence of base KOH to obtain the compound of formula A.

5. The process as claimed in claim 4, wherein said process comprises the step of reacting Rohitukine with a substituted aromatic aldehyde in the presence of KOH for a period from 10 to 20 hrs to obtain compound of formula A.

6. A method for treating a proliferative disorder in a patient in need thereof comprising administering to said patient a compound of formula A or a pharmaceutically acceptable salt thereof,

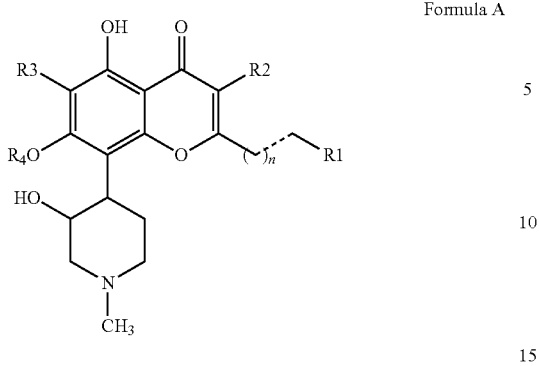

Formula A wherein,
n=1, the dotted line indicates a double bond,
$R_1$ is selected from the group consisting of substituted aryl, fused aryl, heteroaryl, substituted heteroaryl, wherein the substituents are selected from the group consisting of halogen, nitro, amino, substituted amino, hydroxyl, alkoxy, carboxyl, and COO-alkyl C1-C4 wherein alkyl is long chain or branched,
$R_2$, $R_3$ and $R_4$ is hydrogen.

7. The method of claim 6 wherein the a proliferative disorder is selected from the group consisting of breast cancer and leukemia.

\* \* \* \* \*